(12) United States Patent
Staskawicz et al.

(10) Patent No.: US 9,580,726 B2
(45) Date of Patent: Feb. 28, 2017

(54) TOMATO PLANTS COMPRISING TRANSGENIC EVENT BS2-X5

(71) Applicant: Regents of the University of California, Oakland, CA (US)

(72) Inventors: Brian J. Staskawicz, Castro Valley, CA (US); Douglas Dahlbeck, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/447,827

(22) Filed: Jul. 31, 2014

(65) Prior Publication Data

US 2015/0040264 A1 Feb. 5, 2015

Related U.S. Application Data

(60) Provisional application No. 61/860,552, filed on Jul. 31, 2013.

(51) Int. Cl.

| | | |
|---|---|---|
| *A01H 5/08* | (2006.01) | |
| *A01H 1/00* | (2006.01) | |
| *C12N 15/82* | (2006.01) | |
| *A01G 1/00* | (2006.01) | |
| *A01H 1/02* | (2006.01) | |
| *C07K 14/415* | (2006.01) | |
| *C12Q 1/68* | (2006.01) | |
| *C12N 15/00* | (2006.01) | |

(52) U.S. Cl.
CPC ......... *C12N 15/8281* (2013.01); *A01G 1/001* (2013.01); *A01H 1/02* (2013.01); *C07K 14/415* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,262,343 B1 | 7/2001 | Staskawicz et al. |
| 6,762,285 B2 | 7/2004 | Staskawicz et al. |
| 2010/0122376 A1 | 5/2010 | Zipfel et al. |
| 2011/0030087 A1* | 2/2011 | Ramon ............ A01H 5/08 800/268 |

OTHER PUBLICATIONS

Dixon, M., et al., "The Tomato CF-2 Disease Resistance Locus Comprises Two Functional Genes Encoding Leucine-Rich Repeat Proteins," *Cell*, Feb. 9, 1996, vol. 84(9), Cell Press, US.
Horvath, D., et al., "Transgenic Resistance Confers Effective Field Level Control of Bacterial Spot Disease in Tomato," *PLos One*, Aug. 2012, pp. 1-9, vol. 7(8).
Tai, T., et al., "Expression of the Bs2 pepper gene confers resistance to bacterial spot disease in tomato," *Proceedings of the National Academy of Sciences, National Academy of Sciences*, Nov. 23, 1999, pp. 14153-14158, vol. 96(4).

* cited by examiner

*Primary Examiner* — Phuong Bui
(74) *Attorney, Agent, or Firm* — Williams Mullen, PC; David M. Saravitz

(57) ABSTRACT

The invention provides seed and plants of tomato comprising transgenic event Bs2-X5 and progeny thereof comprising this transgenic event and uses of such seeds and plants in the production of tomato fruit. The invention thus relates to non-hybrid and hybrid plants, seeds, and tissue cultures of tomato comprising transgenic event Bs2-X5, and to methods for producing a tomato plant produced by crossing such plants with themselves or with another tomato plant, such as a plant of another genotype. The invention further relates to seeds and plants produced by such crossing. The invention further relates to parts of such plants, including the fruit and gametes of such plants.

17 Claims, 5 Drawing Sheets

US 9,580,726 B2

TOMATO PLANTS COMPRISING TRANSGENIC EVENT BS2-X5

CROSS-REFERENCE TO RELATED APPLICATION

This application claims the benefit of U.S. Provisional Application No. 61/860,552, filed Jul. 31, 2013, which is hereby incorporated herein in its entirety by reference.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 449057SEQLIST.TXT, created on Jul. 31, 2014, and having a size of 20.9 kilobytes, and is filed concurrently with the specification. The sequence listing contained in this ASCII formatted document is part of the specification and is herein incorporated by reference in its entirety.

FIELD OF THE INVENTION

The present invention relates to the field of plant improvement and, more specifically, to the development of tomato plants comprising enhanced resistance to bacterial spot disease.

BACKGROUND OF THE INVENTION

Bacterial spot disease, a complex of four *Xanthomonas* species, is among the most widespread and destructive diseases of tomatoes and peppers throughout the world, causing lesions on aerial plant parts leading to defoliation and fruit loss [1]. It has chronically afflicted U.S. tomato production, particularly in Florida, where the largest production of fresh market tomatoes occurs. Ninety-seven percent of Florida acres are affected, and yield losses may reach fifty percent of marketable production [2].

Various crop protection compounds have been used to control bacterial spot in commercial tomato and pepper production. In the 1950s, streptomycin was commonly used to control plant diseases caused by bacteria, including bacterial spot. *Xanthomonas euvesicatoria* (Race T1), the prevalent bacterial spot race in Florida at the time, quickly became resistant to streptomycin [3], [4], and its use was discontinued. In the 1960s, fixed copper compounds and copper-fungicide mixes became the primary means of bacterial spot control. Initially fixed copper was used alone, but resistance in xanthomonads developed quickly [5]. In response to observing increased efficacy when copper was mixed with ethylenebisdithiocarbamate (EBDC) fungicides such as maneb and mancozeb, growers began mixing fixed copper products with EBDC fungicides for improved bacterial spot control [5]. However, even these copper-fungicide mixes have become ineffective against tomato races of the pathogen, especially under conditions of high humidity and warm temperatures that favor heavy disease pressure (eg [6], [7], [8], [9]; Table 4).

Because crop protection compounds do not control the copper tolerant *Xanthomonas* races responsible for this disease, genetic resistance against bacterial spot has been a priority in tomato breeding programs. These breeding efforts have been slowed by the complex genetics of resistance and changing races of the pathogen, and consequently there are no commercial varieties with effective resistance to *Xanthomonas*. One commonly bred form of plant disease resistance relies on the evolution of specific intracellular immune receptors encoded by disease resistance, or R, genes. R genes have been selected through conventional breeding for over 100 years [10]. They encode specific receptors that recognize gene products made by specific races of a given pathogen species. These pathogen components are termed effectors, and they contribute to pathogen virulence by suppressing or modulating host defenses in susceptible plant genotypes that lack a corresponding R gene [11].

AvrBs2 is an effector that is highly conserved in a number of *Xanthomonas* species that infect a wide range of plant hosts, including tomato [12]. Unlike other key effectors, it is present in all six races of the tomato bacterial spot disease complex (Table 5). Mutations in AvrBs2 can impair virulence, indicating that it plays an important role in pathogenicity and may be a good target for durable resistance [12].

AvrBs2 is recognized by the R protein Bs2, identified in pepper, a fellow member of the Solanaceae and close relative of tomato. Previously, transgenic tomato plants expressing the Bs2 gene were reported to have enhanced resistance to bacterial spot disease following vacuum infiltration of leaves with *Xanthomonas campestris* pv. *vesicatoria* (Xcv) in the laboratory [13]. However, at that time resistance was not assessed under field conditions nor with the prevalent *Xanthomonas* strains that are known to cause bacterial spot disease of tomato.

BRIEF SUMMARY OF THE INVENTION

The present invention provides tomato plants and seeds comprising transgenic event Bs2-X5. Such plants and seeds comprise enhanced resistance to bacterial spot disease caused by *Xanthomonas* species. Parts of these tomato plants are also provided including, for example, leaves, pollen, ovules, stems, scions, rootstocks, fruit, and cells. The present invention further comprises tomato products, preferably products made from tomato fruit including, but not limited to ketchup, tomato juice, tomato paste, tomato sauce, whole and/or chopped canned tomatoes, dried tomato fruit and/or fruit parts, tomato puree, and salsa. Preferably, such parts of tomato plants and tomato products comprise genomic DNA comprising transgenic event Bs2-X5.

The present invention further provides a tissue culture of regenerable cells of a tomato plant comprising transgenic event Bs2-X5. The tissue culture will preferably be capable of regenerating tomato plants capable of expressing all of the physiological and morphological characteristics of the starting plant, and of regenerating plants having substantially the same genotype as the starting plant, and particularly transgenic event Bs2-X5. The regenerable cells in such tissue cultures may be derived, for example, from embryos, meristems, cotyledons, pollen, leaves, anthers, roots, root tips, pistils, flowers, seed and stalks.

Additionally, the present invention provides processes are for producing tomato seeds, plants and fruit, which processes generally comprise crossing a first parent tomato plant with a second parent tomato plant, wherein at least one of the first or second parent tomato plants is a plant comprising transgenic event Bs2-X5. These processes may be further exemplified as processes for preparing hybrid tomato seed or plants, wherein a first tomato plant is crossed with a second tomato plant of a different, distinct genotype to provide a hybrid that has, as one of its parents, a plant comprising transgenic event Bs2-X5. In these processes, crossing will result in the production of seed. The seed production occurs regardless of whether the seed is collected or not. Preferred seeds comprise transgenic event Bs2-X5.

In certain embodiments, the present invention provides a method of producing food or feed comprising: (a) obtaining a plant comprising transgenic event Bs2-X5, wherein the plant has been cultivated to maturity, and (b) collecting at least one tomato from the plant.

SEQUENCE LISTING

Figure 1:
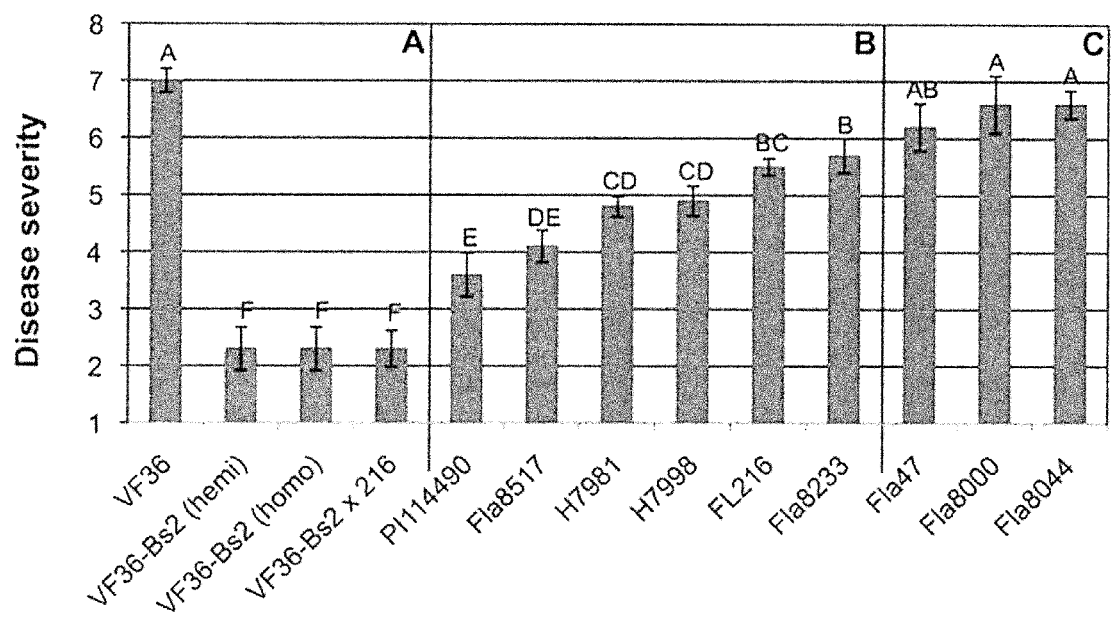
FIG. 1. Comparison of bacterial spot disease severity among transgenic and disease resistant tomato genotypes. Results of field trials in Citra and Balm, Fla., 2006-7. Data are overall mean disease severity scores from three field trials (Table 7). Panel a: VF 36 lines without Bs2 or with one (hemi, and VF36-Bs2×216) or two (homo) copies of the Bs2 gene; Panel b: tomato breeding lines with resistance to bacterial spot disease; Panel c: tomato lines susceptible to bacterial spot. Disease severity was determined by the Horsfall-Barratt defoliation scale (1=0%; 2=0-3%; 3=3-6%; 4=6-12%; 5=12-25%; 6=25-50%; 7=50-75%; 8=75-87%; 9=87-93%; 10=93-97%; 11=97-100%; and 12=100% defoliation) [14]. Error bars denote standard errors of the mean. Letters above bars indicate statistically significant differences in mean values.

The nucleotide and amino acid sequences listed in the accompanying Sequence Listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention provides methods and compositions relating to plants, seeds and derivatives of a tomato plant comprising transgenic event Bs2-X5. As described hereinbelow, such plants and derivatives display enhanced resistance to bacterial spot diseases of tomato caused by *Xanthomonas* species. Plants, seeds, and derivatives comprise in their genomes a transgene comprising a CaMV 35S promoter::Bs2 resistance gene construct as previously described [13]. Also as described herein below, yields of marketable fruit from tomato lines comprising transgenic event Bs2-X5 were typically about 2.5-fold higher than control non-transformed lines lacking transgenic event Bs2-X5. Thus, the present invention provides tomato plants that find use in tomato fruit production in regions where bacterial spot disease is prevalent.

Preferably, the tomato plants and seeds of the invention are of the species *Solanum lycopersicum* (also known as *Lycopersicon esculentum*). However, the present invention includes, but is not limited to, plants comprising transgenic event Bs2-X5 that are of species with the genus *Solanum*, preferably within the subgenus *Lycopersicon*, other than *Solanum lycopersicum*. It is recognized that there are methods known in the art for introducing a transgenic event, such as, for example, transgenic event Bs2-X5, from one plant species to another closely related plant species and that the use of any such methods is encompassed by the present invention. Such methods comprise, for example, cross-pollination, and can optionally further comprise embryo rescue. Closely related plant species include, for example, two species within the same family (e.g. Solanaceae), preferably two species within the same subfamily (e.g. Solanoideae), more preferably two species within the same tribe (e.g. Solaneae), even more preferably two species within the same genus (e.g. *Solanum*), and most preferably two species within the same subgenus (e.g. *Lycopersicon*).

The present invention is drawn to tomato plants comprising transgenic event Bs2-X5. A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Definitions of some additional terms used herein include, but are not limited to, the following definitions:

"Backcrossing" is a process in which a breeder repeatedly crosses hybrid progeny, for example a first generation hybrid (F.sub.1), back to one of the parents of the hybrid progeny. Backcrossing can be used to introduce one or more single locus conversions from one genetic background into another.

"Crossing" is the mating of two parent plants.

"Cross-pollination" is the fertilization by the union of two gametes from different plants.

A "diploid" is a cell or organism having two sets of chromosomes.

"Emasculate" means to remove of plant male sex organs or the inactivation of the organs with a cytoplasmic or nuclear genetic factor or a chemical agent conferring male sterility.

"Enzymes" are molecules which can act as catalysts in biological reactions.

An "F1 Hybrid" is the first generation progeny of the cross of two nonisogenic plants.

A "genotype" is the genetic constitution of a cell or organism.

A "haploid" is a cell or organism having one set of the two sets of chromosomes in a diploid.

"Linkage is a phenomenon wherein alleles on the same chromosome tend to segregate together more often than expected by chance if their transmission was independent.

A "Marker" is a readily detectable phenotype, preferably inherited in codominant fashion (both alleles at a locus in a diploid heterozygote are readily detectable), with no environmental variance component, i.e., heritability of 1.

A "phenotype" is the detectable characteristics of a cell or organism, which characteristics are the manifestation of gene expression.

"Quantitative Trait Loci (QTL)" refer to genetic loci that control to some degree numerically representable traits that are usually continuously distributed.

As used herein, the terms "resistance" and "tolerance" are used interchangeably to describe tomato plants that show no or lesser symptoms to a bacterial spot disease caused by *Xanthomonas* species when compared to a control plant lacking transgenic event Bs2-X5. These terms are also used to describe plants showing some symptoms but that are still able to produce marketable product with an acceptable yield.

"Regeneration" is the development of a plant from tissue culture.

"Self-pollination" is the transfer of pollen from the anther to the stigma of the same plant.

A "Single Locus Converted (Conversion) Plant" is a plant which is developed by a plant breeding technique called backcrossing, wherein essentially all of the morphological and physiological characteristics of a tomato variety are recovered in addition to the characteristics of the single locus transferred into the variety via the backcrossing technique and/or by genetic transformation.

"Substantially Equivalent" is a characteristic that, when compared, does not show a statistically significant difference (e.g., p=0.05) from the mean.

"Tissue Culture" is a composition comprising isolated cells of the same or a different type or a collection of such cells organized into parts of a plant.

A "transgene" is a genetic locus comprising a sequence which has been introduced into the genome of a plant by transformation.

Additional terms concerning the present invention are defined elsewhere herein above and below.

The tomato plants of the present invention are derived from a single transgenic event comprising the insertion of a construct containing a CaMV 35S promoter::Bs2 resistance gene into the genome of a VF36 tomato plant. This transgenic event is referred to herein as transgenic event Bs2-X5. It has been determined that the construct has inserted into the SL2.40ch10 location of the tomato genome (Sol Genome Network). The genomic flanking region adjacent to the left border of the insert comprising the following nucleotide sequence in the 5' to 3' direction:

```
                                            (SEQ ID NO: 1)
CAAGTGCAACACAAATTAGGACAATAATATGAATTGAAGACTAAAAA

GTAAAAATAATAACTAATAGTTAAAATTACAATCGAATTGATAACCCT

ATAATTTATTTTATAAAA.
```

Given that this adjacent flanking genomic region of transgenic event Bs2-X5 is known, a plant comprising this event can be identified by, for example, polymerase chain reaction (PCR) amplification using a suitable primer pair for amplification of a DNA fragment comprising the novel junction between the flanking region and the insert DNA. Thus, the invention provides methods for identifying transgenic event Bs2-X5 in tomato plants and other plants. Such methods involve using a DNA from a tomato plant and conducting PCR amplification using a pair of primers designed to detect a novel junction between the flanking region and the insert DNA. Such a pair of primers can comprise, for example, a first primer designed to anneal to a sequence within the flanking region (e.g. SEQ ID NO: 1 and/or SEQ ID NO: 41) or its complement and a second primer that is designed to anneal to the sequence within the insert or its complement. Such sequences within the insert include, but are not limited to, sequences within the CaMV 35S promoter::Bs2 resistance gene construct (SEQ ID NO: 42) and the left border (LB) and right border (RB) T-DNA sequences (SEQ ID NOS: 43 and 44, respectively) surrounding the CaMV 35S promoter::Bs2 resistance gene. These sequences are provided in Sequence Listing. Also provided in the Sequence Listing are SEQ ID NOS: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. SEQ ID NOS: 2-40 are examples of some suitable PCR primer sequences that can be used in the methods of the present invention for identifying transgenic event Bs2-X5 in tomato plants and other plants and the names of these primers are provided in Table 1. However, it is recognized the methods of the present invention do depend on a particular pair of primers and methods for primer design for PCR amplification of a DNA fragment of interest are known in the art. Thus, the present invention encompasses the use of pair of primers comprising a first primer designed to anneal to a nucleotide sequence within the flanking region or its complement and a second primer that is designed to anneal to a nucleic acid sequence within the insert or its complement can be used in the methods disclosed herein.

TABLE 1

PCR Primers for Identification of Transgenic Event Bs2-X5

| SEQ ID NO | Primer |
|---|---|
| 2 | BS2 Fw1428 |
| 3 | BS2 Rev 1868 |
| 4 | BS2 Fw1742 |
| 5 | BS2 Rev2560 |
| 6 | BS2 Fw2460 |
| 7 | BS2 Fw2600 |
| 8 | BS2 Rev 2718 Spe-Stop-Xba |
| 9 | pMD-BS2 Fw1400-RB |
| 10 | pMD-BS2 Rev1440-RB |
| 11 | pMD-BS2 Fw2100-RB |
| 12 | pMD-BS2 Rev2200-RB |
| 13 | RB Rev |
| 14 | NPT2 Rev1 |
| 15 | NPT2 Rev2 |
| 16 | LB Fw |
| 17 | BS2 term Fw1500 |
| 18 | M13 Fw-Rev |
| 19 | NPT2 Fw2 |
| 20 | RB-Rev2 |
| 21 | RB-pMDinvRev |
| 22 | RB-pMDinvFw |
| 23 | LB-pMDinvFw |
| 24 | LB-pMDinvRev |
| 25 | NosPro Fw |
| 26 | NPT2 Rev3 |
| 27 | NosPro Fw-2 |
| 28 | pMD-BS2 Sau3A in-RB |
| 29 | MD-BS2 Sau3A out-RB |
| 30 | pMD-BS2 Sau3A out-RB-2 |
| 31 | pMD-BS2 Sau3A in-LB-1 |
| 32 | pMD-BS2 Sau3A in-LB-2 |
| 33 | pMD-BS2 Sau3A out-LB-2 |
| 34 | pMD-BS2 Sau3A out-LB-3 |
| 35 | pMD-BS2 Sau3A out-LB-1 |
| 36 | X5 Flnk LB Rev 1500 |
| 37 | X5 Flnk LB Rev 1000 |
| 38 | X5 Flnk RB Fw 750 |
| 39 | X5 Flnk RB Fw 1500 |
| 40 | pMD-BS2 out-RB-3 |

If the tomato plant comprises transgenic event Bs2-X5, then a DNA fragment of the expected size will be produced by the PCR amplification with a pair of primers comprising a first primer designed to anneal to genomic DNA in a flanking region on either side of the insert DNA and a second primer designed to anneal to insert DNA. If the tomato plant does not comprise transgenic event Bs2-X5, then no DNA fragment of the expected size will be produced by PCR amplification with such a pair of primers. In other embodiments, the pair of primers can comprise first primer designed to anneal to genomic DNA in a flanking region on one side (e.g. left side) of the insert DNA and a second primer designed to anneal to the flanking region on the other side (e.g. right side) of the insert DNA, whereby a DNA fragment of the expected size and comprising the entire insert and flanking genomic DNA on both sides of the insert is produced when genomic DNA from plants comprising transgenic event Bs2-X5 is subjected to PCR amplification. If the tomato plant does not comprise transgenic event Bs2-X5, then no DNA fragment of the expected size will be produced by PCR amplification with such a pair of primers.

In a PCR approaches, oligonucleotide primers can be designed for use in PCR reactions to amplify corresponding nucleic acid molecules from cDNA or genomic DNA extracted from any organism of interest. Methods for designing PCR primers and PCR amplification are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

One aspect of the current invention concerns methods for producing new tomato lines and hybrids with enhanced resistance to bacterial spot disease and comprising transgenic event Bs2-X5. The methods involve crossing first tomato plant comprising transgenic event Bs2-X5 with a second tomato plant lacking comprising transgenic event Bs2-X5. The first plant can be homozygous or hemizygous for transgenic event Bs2-X5. However, in preferred embodiments the first plant is homozygous for transgenic event Bs2-X5 whereby all F1 progeny of the crossing will comprise transgenic event Bs2-X5. If the first plant is hemizygous for transgenic event Bs2-X5, then the method can comprise the optional step of selecting for the presence of the transgenic event Bs2-X5 using, for example, the PCR approach described above or functional assays previously described [13].

The development of new varieties using one or more starting lines is well known in the art. In accordance with the invention, novel varieties may be created by crossing a tomato plant comprising transgenic event Bs2-X5 with a second tomato plant followed by multiple generations of breeding according to methods well known in the art and/or described elsewhere herein. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines with enhanced resistance to bacterial spot disease. In selecting a second plant to cross with a first plant comprising transgenic event Bs2-X5 for the purpose of developing novel tomato lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of tomato plants developed by this invention.

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those tomato plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. For the present invention, the parental tomato plant which contributes transgenic event Bs2-X5 is termed the nonrecurrent or donor parent. This terminology refers to the fact that the nonrecurrent parent is used one time in the backcross protocol and therefore does not recur. The parental tomato plant to which transgenic event Bs2-X5 from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest (e.g. transgenic event Bs2-X5) to be transferred. The resulting progeny from this cross are then crossed again to the recurrent parent and the process is repeated until a tomato plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny tomato plants of a backcross in which a plant described herein is the recurrent parent comprise (i) the desired trait from the non-recurrent parent and (ii) all of the physiological and morphological characteristics of tomato the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for bacterial resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs).

The tomato plants comprising transgenic event Bs2-X5 find particular use in commercial tomato production in areas in which bacterial spot disease is prevalent and provide increased yields of tomato fruit compared to tomato fruit production with tomato plants lacking transgenic event Bs2-X5. Thus, the present invention further provides methods for increasing tomato fruit production in areas in which bacterial spot disease is known to occur. The method comprises growing one or more tomato plants comprising transgenic event Bs2-X5 under conditions favorable for the development of bacterial spot disease. Typically, the tomato plants are grown outdoors in agricultural fields but the methods of the invention can also be used with tomato plants grown under greenhouse conditions or under other indoor or controlled-environment conditions. The tomato plants are allowed to grow and produce mature tomato fruit and then the fruit are harvested from the plants. The methods provide for an increase in tomato fruit yield in the presence of bacterial spot disease when compared to the tomato fruit yield of control tomato plants but grown under the same or similar conditions.

The control tomato plants lack the tomato plants comprising transgenic event Bs2-X5 comprise enhanced resistance to bacterial spot disease relative to the control tomato plant lacking transgenic event Bs2-X5. Preferably, the control tomato plants are of the same or essentially the same genotype (except for they lack transgenic event Bs2-X5) as the tomato plants comprising transgenic event Bs2-X5.

A deposit of at least 2500 tomato seeds comprising transgenic event Bs2-X5 disclosed above and recited in the claims, was made with the American Type Culture Collection (ATCC), 10801 University Blvd., Manassas, Va. 20110-2209, and the deposit was assigned ATCC Patent Deposit No. PTA-121404. The deposit date is Jul. 17, 2014. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112. Upon issuance of a patent, all restrictions upon the deposits will be removed, and the deposits are intended to meet all of the requirements of 37 C.F.R. §§1.801-1.809. The deposits will be maintained in the depository for a period of 30 years, or 5 years after the last request, or for the effective life of the patent, whichever is longer, and will be replaced if necessary during that period.

EXAMPLES

Example 1

Transgenic Resistance Confers Effective Field Level Control of Bacterial Spot Disease in Tomato In this example Bs2 transgenic tomato lines were field tested and shown to be effective against current field races of bacterial spot in multi-year field trials conducted in two commercial growing regions of Florida. All Bs2 transgenic lines and/or tomato plants described in Example 1 comprise transgenic event Bs2-X5, which comprises the Bs2 gene. The results demonstrate that tomatoes carrying the Bs2 gene, in transgenic event Bs2-X5 and which received no bactericidal crop protection compounds had the highest disease resistance of all the genotypes tested and had significantly increased yields relative to controls.

Results

All Field Strains of Bacterial Spot are Recognized by Plants Carrying the Resistance Gene Bs2

We assessed *Xanthomonas* populations on tomato plants across the state of Florida, and partly into Georgia, to examine the race structure and prevalence of key effectors. We tested 377 samples collected across all five commercial tomato production regions and made race determinations based on the elicitation of a hypersensitive reaction (HR) on plant genotypes carrying R genes that specifically recognize key effectors present in certain *Xanthomonas* races (Table 6). Two of the six known tomato bacterial spot races were found (Table 2). These were the highly related *X. perforans* strains that are distinguished into separate races based on the presence (race T3) or absence (race T4) of the effector AvrXv3. AvrXv3 triggers an HR on T3-resistant tomato lines carrying the Xv3 locus, thus race T4 overcomes resistance on these lines. 115 of the 377 strains (30%) were found to be race T3, and the remaining 70% (262 strains) were race T4. All strains elicited an HR on the Bs2 genotype, indicating the presence of AvrBs2.

TABLE 2

Survey of bacterial spot strains isolated from tomato plants throughout Florida production zones.

| County | Production Zone | Fruit type | # Strains isolated | Bonny Best (Susc) | H7998 (Rxv) | FL216 (Xv3) | 3X-2-4 (Xv4) | VF36-Bs2 (Bs2) | ECW pepper | Race determinations[b] T3 | T4 | Bactericide Resistance[c] St | Cu |
|---|---|---|---|---|---|---|---|---|---|---|---|---|---|
| Miami Dade | I | Large Fruit | 15 | 0 | 0 | 0 | 15 | 15 | 15 | 0 | 15 | 0 | 15 |
| Miami Dade | I | Large Fruit | 20 | 0 | 0 | 0 | 20 | 20 | 20 | 0 | 20 | 19 | 20 |
| Miami Dade | I | Large Fruit | 13 | 0 | 0 | 0 | 13 | 13 | 13 | 0 | 13 | 0 | 13 |
| Miami Dade | I | Plum | 20 | 0 | 0 | 19 | 20 | 20 | 20 | 19 | 1 | 0 | 20 |
| Palm Beach | II | Heirloom varieties | 14 | 0 | 0 | 0 | 14 | 14 | 14 | 0 | 14 | 0 | 14 |
| Collier | III | Florida 47 | 20 | 0 | 0 | 6 | 20 | 20 | 20 | 6 | 14 | 0 | 20 |
| Collier | III | Roma | 20 | 0 | 0 | 8 | 20 | 20 | 20 | 8 | 12 | 0 | 20 |
| Collier | III | Grape | 20 | 0 | 0 | 0 | 20 | 20 | 20 | 0 | 20 | 0 | 20 |
| Collier | III | Grape | 18 | 0 | 0 | 0 | 18 | 14 | 14 | 0 | 18 | 0 | 14 |
| Collier | III | Large Fruit | 19 | 0 | 0 | 1 | 19 | 19 | 19 | 11 | 8 | 0 | 19 |
| Manatee | IV | Large Fruit | 20 | 0 | 0 | 2 | 20 | 20 | 20 | 2 | 18 | 0 | 20 |
| Manatee | IV | Large Fruit | 20 | 0 | 0 | 5 | 20 | 20 | 20 | 5 | 15 | 0 | 20 |
| Manatee | IV | Large Fruit | 20 | 0 | 0 | 15 | 20 | 20 | 20 | 15 | 5 | 0 | 20 |
| Manatee | IV | Large Fruit | 20 | 0 | 0 | 5 | 20 | 20 | 20 | 5 | 15 | 1 | 20 |
| Manatee | IV | Large Fruit | 20 | 0 | 0 | 4 | 20 | 20 | 20 | 4 | 16 | 0 | 20 |
| Gadsden | V | Large Fruit | 20 | 0 | 0 | 10 | 20 | 20 | 20 | 10 | 10 | 0 | 20 |
| Gadsden | V | Large Fruit | 19 | 0 | 0 | 9 | 19 | 19 | 19 | 9 | 10 | 0 | 19 |
| Decatur, GA | V | Large Fruit | 19 | 0 | 0 | 15 | 19 | 19 | 19 | 15 | 4 | 0 | 19 |
| Decatur, GA | V | Large Fruit | 20 | 0 | 0 | 0 | 20 | 20 | 20 | 0 | 20 | 0 | 20 |
| Decatur, GA | V | Large Fruit | 20 | 0 | 0 | 6 | 20 | 20 | 20 | 6 | 14 | 0 | 20 |
| Totals | | | 377 | 0 | 0 | 115 | 377 | 377 | 377 | 115 | 262 | 20 | 377 |

[a] Plant lines and their relevant genotype (in parentheses) used for testing are listed in Table 6.
[b] Race determinations were based on HR elicited in by effectors listed in Table S2.
[c] Bactericides tested were Streptomycin (St) and copper (Cu). Numbers denote resistant strains.

Bs2 Confers No Adverse Effects

The transgenic VF 36 lines containing Bs2 from pepper were previously characterized and described [13]. The lines have a single transgene insertion, and sequencing of the transgenic locus confirmed the expected sequence of the gene construct as reported. Because detection of Bs2 mRNA is difficult, confirmation of transgene expression has been based on bioassays (bacterial growth curves and hypersensitive reaction (HR)) in transiently and stably transformed lines. Besides the effects on disease resistance and yield reported in the current study, no other effects of the Bs2 gene were observed on general growth, development, morphology or other horticultural characteristics of plants. Similar results were observed with other Bs2 lines in the VF 36 background and also five other tomato varieties into which the gene has been introduced as described below.

Bs2 Transgenic Resistance Confers the Highest Level of Disease Resistance Among Bacterial Spot-Resistant Tomato Genotypes In a study comprised of three trials comparing thirteen tomato genotypes that included the best available resistant breeding lines, transgenic Bs2 tomato lines consistently had the lowest disease symptoms in the presence of high *X. perforans* disease pressure (FIG. 1, Table 7). Whereas the non-transformed VF 36 line was the most susceptible with the highest disease severity score of 7, VF 36 lines carrying the Bs2 gene had the lowest disease severity, with a rating of 2.3 (FIG. 1A). Transgenic lines that were hemizygous or homozygous for Bs2 had the same disease severity scores, as did the $F_1$ hybrid of VF 36-Bs2 crossed with FL216. Intermediate levels of disease severity were measured in several lines selected for conventional resistance to *Xanthomonas* with scores between 3.6 and 5.7 (FIG. 1B). Notably the plant introduction accession PI 114490 showed the lowest disease severity of non-transgenic lines. This accession is used in several breeding programs, however successful transfer of its resistance loci into commercial varieties has not yet been accomplished. The lines Fla47, Fla. 8000, and Fla. 8044 were highly susceptible in our trials with scores between 6.2 and 6.7 (FIG. 1C).

The measure of disease severity was the extent of bacterial spot symptoms on all plants in a plot, assessed using the Horsfall-Barratt scale [14]. Low levels of disease appeared as a small number of leaf spot lesions on a few leaves, with little defoliation. More extensive disease appeared as increasing numbers of lesions on a greater numbers of leaves, stems, and sometimes fruit. In the most severe cases, entire leaves or leaflets browned and dessicated from closely spaced lesions and associated necrosis.

Figure 2:
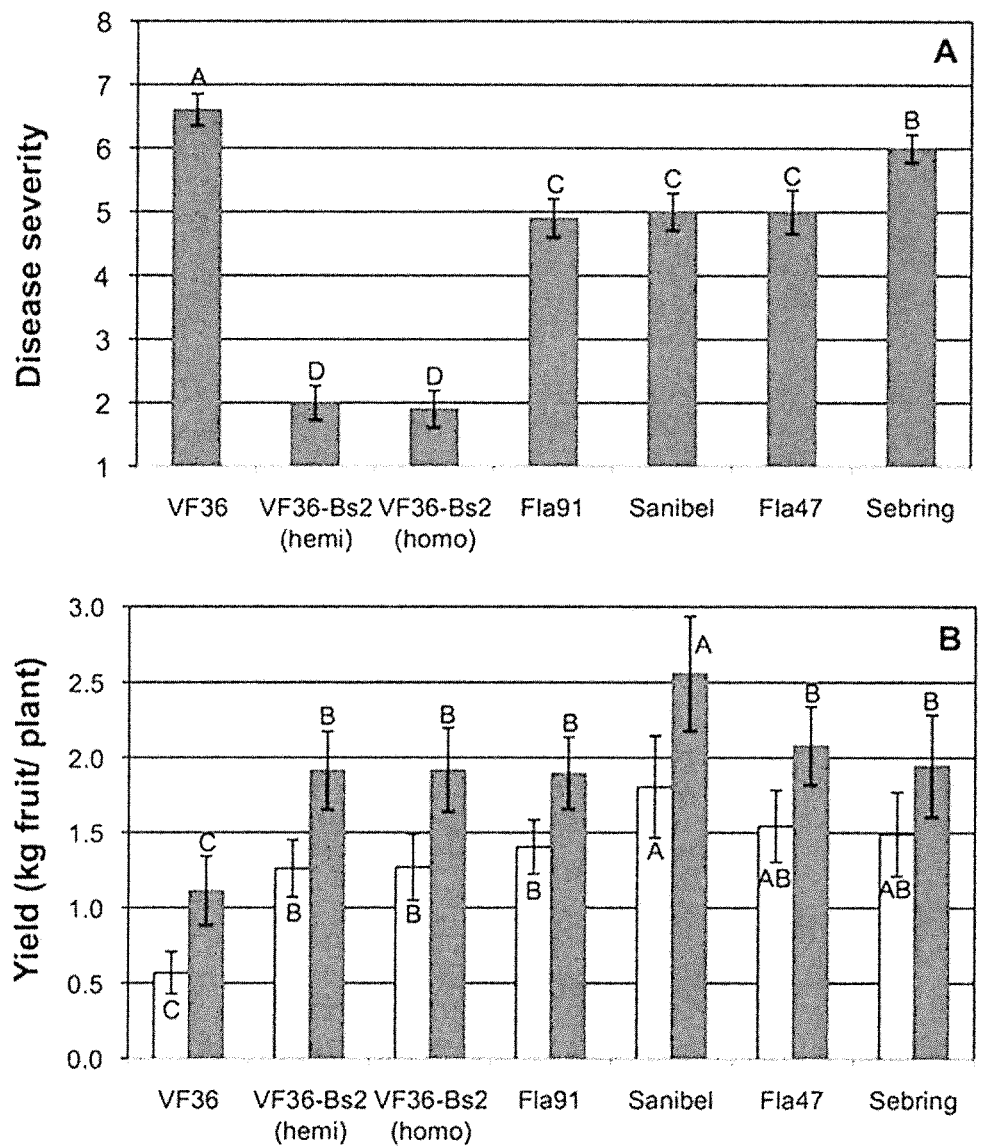
FIG. 2. Comparison of disease severity and yield in transgenic and commercial tomato varieties. Results from Balm, Fla., field trials, 2007-2010. Data shown are the combined analysis of five trials (Table 9), derived from the individual trial results given in Table 8. a: Bacterial spot disease severity. Disease severity was determined by the Horsfall-Barratt defoliation scale (See FIG. 1 legend) [14]. Error bars denote standard errors of the mean. Letters above bars indicate statistically significant differences in mean values. b: Yield. Marketable yield (open bars) is kg per plant for medium, large, and extra large fruit. Total yield (filled bars) is kg per plant for marketable yield plus small fruit and culls. VF 36 lines have no (VF36), one (VF36-Bs2 hemi) or two (VF36-Bs2 homo) copies of the Bs2 gene. Error bars denote standard errors of the mean. Letters above bars indicate statistically significant differences in mean values for total yield data, whereas letters below bars indicate significant differences in mean values for marketable yield data.

The Bs2 Gene Confers a Substantial Yield Improvement Under High Disease Pressure In a second study to make performance comparisons between Bs2 transgenic lines and standard commercial varieties, five trials were carried out to assess disease severity and yield impact (FIG. 2, Tables S5 (individual trial results) and S6 (combined trial results). As shown in FIG. 2A, the lowest level of disease severity in these trials was again observed on transgenic lines, with scores of 2.0 and 1.9, for hemizygous and homozygous Bs2 lines, respectively, contrasted with the high susceptibility of the non-transformed VF 36 line with a disease severity score of 6.6. All four of the commercial lines displayed appreciable disease symptoms with ratings between 4.9 and 6. In yield comparisons, the addition of Bs2 into the VF 36 background substantially increased marketable and total yields of this un-adapted California variety to levels comparable to commercial Florida varieties (FIG. 2B). VF 36 had the lowest marketable and total fruit yields of all the lines used in the trials, but the presence of Bs2 in the VF 36 background boosted marketable yield from 0.06-1.49 kg/plant to 0.49-2.47 kg/plant, and total yields were increased from 0.12-2.40 kg/plant to 0.67-3.29 kg/plant.

Comparisons with non-inoculated, disease free plants were not possible under Florida field conditions where the disease is endemic.

Bs2 Confers a Positive Yield Effect Even Under Low Disease Pressure

We considered the effect of temperatures and total rainfall on the five field experiments in Balm, Fla. (Table 10). Monthly temperatures were generally within 5% of seven-year averages, whereas rainfall was more variable, being either average, higher or lower than average, or seasonally average but unevenly distributed. Together with weather data, we considered the observed disease severity (pressure) and marketable yields (Table 8) to determine an impact factor for Bs2 in the VF 36 background (Table 3). Bs2 typically conferred a yield enhancement of 2.5-2.8-fold and, in one season, a more than 10-fold increase. Even under very low disease pressure, VF 36-Bs2 lines displayed a 1.5-fold enhancement of marketable yield compared to VF 36 lines.

DISCUSSION

Bacterial spot disease has been a serious issue in tomato production for more than sixty years, and the commercial industry has been unable to control it via the extensive use of chemical, genetic, and cultural methods. We have investigated the potential of transgenic control of bacterial spot using the pepper Bs2 gene in seven field trials under typical commercial growing conditions. The Bs2 gene was identified more than two decades ago as an exceptional disease resistance candidate for transfer to tomato, because it activates resistance following specific recognition of AvrBs2, a *Xanthomonas* effector that is highly conserved in tomato races and races affecting other crops [12]. Despite periodic shifts in *Xanthomonas* races on field tomatoes and the expulsion or mutation of some effectors such as AvrXv3 under selection pressure, our survey showed that all current field isolates expressed active AvrBs2. Therefore, Bs2 resistance targeted to AvrBs2 should be broadly effective.

The purpose of the current study was to examine the performance of selected Bs2 lines under field conditions. Many publications on transgenic field trials report data at single locations, replicated, on average, over three seasons [15], [16], [17], [18], [19], [20], [21]. To provide a comprehensive view of Bs2 field performance, we report seven trials in two locations on studies comparing (i) disease resistance relative to a set of genotypes with varying levels of resistance and (ii) disease resistance and yield relative to widely grown commercial cultivars. Trials were carried out in commercial growing zones IV (Balm) and V (Citra), where 32% and 6%, respectively, of Florida fresh market tomato production takes place.

We compared the disease severity of a range of tomato genotypes including standard commercial varieties, the best available spot resistant breeding lines, and Bs2 transgenic lines. The non-transformed parent line VF 36 was the most susceptible to *X. perforans* infection including race T4, the predominant field race. The commercial cultivars Fla47, Fla91, Sebring and Sanibel were also highly susceptible. The plant introduction and inbred lines tested did express lower disease severity, however these lines have not been optimized for horticultural characteristics and require further breeding. VF 36 lines containing Bs2 consistently exhibited the lowest bacterial spot disease symptoms of all genotypes and were generally free of characteristic lesions and defoliation.

In yield studies, Bs2 had a significant positive impact on marketable and total yields. Whereas non-transformed VF 36 performed most poorly, with as little as one third of the production of Florida varieties, the presence of Bs2 in the

TABLE 3

Summary of field trial conditions at Balm, FL, and Bs2 impact factor.

| | Fall 2007 | Spring 2008 | Fall 2008 | Spring 2009 | Fall 2010 |
|---|---|---|---|---|---|
| Temperature[a] | Normal, hot late | Normal | Normal | Normal | Normal, cool late |
| Rainfall[b] | Average, uneven | Low-average | Low | Many wks 4-8 | Very low |
| Disease pressure[c] | High | High | Low | High | Very low |
| Yield[d] | Low | Medium | Low-medium | Med-high | Very high |
| Bs2 impact factor[e] | 11.8 | 2.8 | 2.5 | 2.6 | 1.5 |

[a]Normal: within 5% of typical averages (Table 10).
[b]Rainfall relative to typical monthly totals (Table 10).
[c]Relative disease pressure based on disease ratings in Table 8. High: VF 36 ratings above 7, commercial lines above 5; Low: VF 36 ratings below 6, commercial lines below 5.
[d]Relative yield summary based on marketable yields in Table 8. Low: 1-2 lbs/plant; Medium: 2.5-3.5 lbs/plant; High" 4.5-6 lbs/plant. Fall 2008 estimates were approximated by doubling yield from single harvest.
[e]Bs2 impact was calculated by dividing the larger of the two values for marketable yield for VF36-Bs2 homo- or hemizygous plants with the marketable yield for VF 36 plants (Table 8).

VF 36 background increased yields to levels comparable to commercial Florida varieties. These results are consistent with studies in pepper in which conventionally-bred bell and hot pepper varieties with the Bs2 locus were found to have lower disease severity and higher fruit yields in trials compared to non-Bs2 varieties [22], [23]. Both genetic background and weather conditions can effect disease severity and yield performance. However, despite varying environmental conditions across the trials, the presence of Bs2 in the VF 36 background typically gave a 2.5-fold or greater increase in marketable yield.

The VF 36 tomato variety is highly susceptible to bacterial spot and not adapted to Florida growing conditions. It has been useful for proof of concept studies and for examining field performance of the trait, but it is not intended for commercial development. We have introduced the Bs2 gene construct used in the current study, as well as others, into commercial tomato parent lines and hybrids from the University of Florida breeding program. Disease responses in the greenhouse and field fully replicate results with VF 36 lines, and preliminary field trials results demonstrate comparable yield increases in the Florida-adapted varieties (unpublished data). Yield increases of this magnitude are highly significant for tomato production in Florida.

Figure 3:
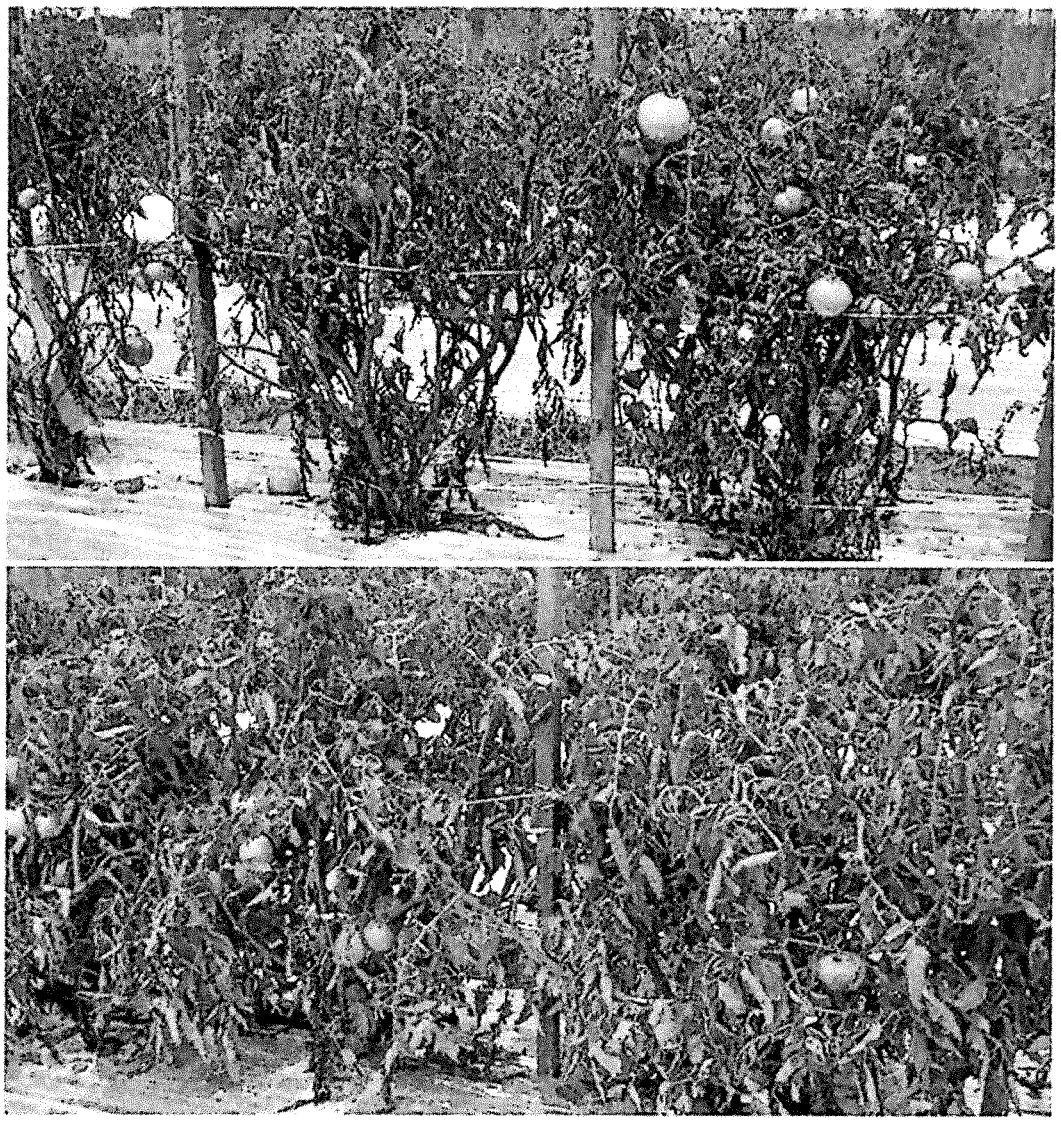
FIG. 3. Photographs of non-transgenic and Bs2-transgenic VF36 lines in field trials. Upper panel: plants of the non-transformed VF36 line. Bottom panel: plants of the transgenic VF36 line containing the 35S:Bs2 gene. Balm, Fla., Spring 2008 Trial. The transgenic Bs-2 lines comprise transgenic event Bs2-X5.
Figure 4:
FIG. 4. Photographs of non-transgenic and Bs2-transgenic Fla. 8314 lines in field trials. Upper panel: plants of the non-transformed Fla. 8314 line. Bottom panel: plants of the transgenic Fla. 8314 line containing the 35S:Bs2 gene. Balm, Fla., Spring 2012 Trial. The transgenic Bs-2 lines comprise transgenic event Bs2-X5.
Figure 5:
FIG. 5. Photographs of non-transgenic and Bs2-transgenic Fla. 8000 lines in field trials. Upper panel: plants of the non-transformed Fla. 8000 line. Bottom panel: plants of the transgenic Fla. 8000 line containing the 35S:Bs2 gene. Balm, Fla., Spring 2013 Trial. The transgenic Bs-2 lines comprise transgenic event Bs2-X5.

Yield differences may result from bacterial spot damage during early growth of tomato plants. In seasons that had hot, wet conditions conducive to infection during the first four to eight weeks that plants were in the field, the greatest spotting and defoliation were routinely observed. Later in the season, even heavily diseased plants tended to outgrow the disease, so that the lower half of the plants were often largely defoliated while the upper half had healthy foliage and fruit production (FIG. 3, top). The net result was that fruit set on the bottom half of each plant was significantly impaired, reducing yield. In contrast, transgenic plants had full foliage and fruit set throughout the plant (FIG. 3, bottom). The current data do not allow us to distinguish if the observed yield increases are a direct effect of disease reduction by Bs2 or if a separate mechanism is contributing to yield. That distinction would have to be made by evaluating yield differences caused by Bs2 in the absence of bacterial spot. Due to the endemic nature of the disease in Florida, it is not possible to grow disease free plants in field trials, and so it could not be tested in the current study. Such a study would require a crop production greenhouse that excludes bacterial spot.

Our results show that transgenic disease resistance is an effective means of controlling bacterial spot. Given that all current field strains were found to be resistant to copper, it is clear why copper compounds have become ineffective for bacterial spot control, yet the lack of alternative measures has resulted in the continued broad use of copper pesticides. We note that streptomycin resistant strains were found in two of our survey collection areas, indicating renewed use of this bactericide in some fields. Given the rapid spread of resistance in the 1950s among *X. euvesicatoria* strains, it's likely that any continued use of streptomycin will lead to resistance among current *X. perforans* strains as well.

Chemical control methods for bacterial spot are not simply ineffective but potentially hazardous as well. Frequent widespread application of copper compounds on tomatoes and citrus has caused persistent high levels of copper in Florida soils, which can leach into streams and ground water [24]. Levels are known to accumulate in wastewater from washing tomatoes at packing houses [25], exceeding safe drinking water limits established by the U.S. Environmental Protection Agency (http://water.epa.gov/drink/contaminants/basicinformation/copper.cfm). In fact fixed copper compounds are amongst the oldest and most toxic crop protection compounds used in both conventional and organic agriculture (www.nysipm.cornell.edu/publications/eiq/files/EIQ_values_2010.pdf). Certainly crop protection compounds play a crucial role in global food production, however safer alternatives must be sought for chemicals that are ineffective or hazardous. In light of the environmental and health issues associated with copper compounds and the fact that transgenic disease resistant papaya and squash have been commercially available and safely consumed for more than a decade [26], one must consider that transgenic disease resistance may provide an improved means of controlling bacterial spot.

Our study is the first demonstration of transgenic resistance in replicated multi-year field trials based on the use of a plant R gene. The Bs2 R protein is a member of the nucleotide binding site-leucine-rich repeat (NB-LRR) family of innate immune receptors [13], one of the largest families of plant proteins [27], [28]. Because Bs2 occurs in pepper, the Bs2 protein, like many NB-LRR proteins, has been widely consumed with no known toxicity or allergenicity. The risk of transgene escape is low, because tomato is >99% self-pollinating [29] and no sexually compatible relatives occur in North America. These features suggest a good safety profile for Bs2 transgenic tomatoes, but before a commercial product can be released all appropriate regulatory studies and requirements will be fulfilled.

Transgenic Bs2 tomatoes provide a feasible alternative for improving both yields and tomato production practices in areas of chronic bacterial spot infection. Proper stewardship of this useful trait should include combining it with other resistance genes for bacterial spot. Even though AvrBs2 is an important contributor to pathogenicity, deployment of Bs2 will put pressure on *Xanthomonas* strains to evolve this effector to overcome resistance. Indeed strains have been isolated with AvrBs2 mutations that recover the ability to grow on pepper and tomato plants carrying the Bs2 gene [30], [31], [32]. However these strains show impaired virulence on both hosts in the presence and absence of Bs2, retain wild-type copies of the gene in populations, and may be unable to compete in the field with wild-type strains. Regardless of the potential for durability of Bs2, or indeed any disease resistance gene, we strongly advocate deploying it in a genetic background with good general disease resistance and with additional specific resistance genes, preferably stacked at a single locus. Finally, use of cultural practices to minimize spread of the pathogen will continue to be important in limiting the impact of bacterial spot.

Materials and Methods

Plant Lines

Plant lines used in this study are listed in Table 6. Transgenic tomato plants were as described [13] using the VF 36 variety transformed with the pepper Bs2 cDNA sequence driven by the CaMV 35S promoter. Three transgenic lines were used, a homozygous VF 36-Bs2 line, a hemizygous VF 36-Bs2 line, prepared by backcrossing the homozygous line to VF 36, and an additional cross of the VF 36-Bs2 line with Florida 216 (FL216), producing VF 36-Bs2×216. Commercial tomato varieties used in trials were Florida 47 (Fla47), Florida 91 (Fla91), Sebring and Sanibel. Experimental inbred lines, Hawaii 7998 and 7981 (H7998, H7981) and plant introduction accessions, PI 114490 and PI 128216, or their derivatives (FL216, produced by crossing PI 128216 with Fla7060) with reported resistance to *Xanthomonas* were also used in trials. The University of Florida breeding program supplied four inbred lines (Fla. 8000, Fla. 8044, Fla. 8233, Fla. 8517) that were included in trials. For the survey of bacterial strains, the tomato lines Bonny Best, H7998, FL216, 3x-2-4, and VF 36-Bs2, and the pepper variety Early Calwonder (ECW) were used to identify bacterial races. The tomato variety Bonny Best is susceptible to *Xanthomonas*, whereas tomato lines H7998, FL216, 3x-2-4, and VF 36-Bs2 contain resistance loci Rxv, Xv3, Xv4, and Bs2, respectively [13], [33], [34], [35], [36], [37]. These resistance loci trigger a hypersensitive reaction (HR) in response to strains containing the corresponding effectors AvrRxv, AvrXv3, AvrXv4, and AvrBs2, respectively. Differential HR results were used to determine which effectors were present in each strain (Table 5) and permit the identification of the race. The pepper variety ECW can distinguish between strains that can grow on pepper (T1, T2 and *X. gardneri*) or cannot (T3-5).

Field Survey of Florida *Xanthomonas* Strains

Bacterial samples were isolated from bacterial spot lesions from twenty different leaflets per field, randomly collected from twenty unique field locations throughout the five major production zones in Florida between October and December, 2006. Production zone V extends partially into Georgia. Three hundred seventy-seven individual isolates were grown on nutrient agar for 24 hr at 28° C., and bacterial cells were removed and suspended in sterile tap water. Suspensions were adjusted to a concentration of $10^8$ cfu/ml and inoculated by infiltration using a hypodermic needle and syringe on to a panel of tomato and pepper plants of varying resistance genotypes (Tables 1 and S3). Each plant was scored as producing a hypersensitive reaction (HR) after 1-2 days, or as producing disease at 3 days.

The bacterial isolates were also tested for sensitivity to the bactericides, streptomycin and copper using established procedures. All strains were tested for growth on media with either streptomycin sulfate (200 µg/ml) or copper sulfate (pentahydrate) 200 µg/ml (0.8 mM)) after 3 days [3], [38].

Field Trials, Inoculation and Assessment

Tomato plants were seeded in a greenhouse and grown for 4-6 weeks prior to transplanting to the field. Young plants were either inoculated with *X. perforans* strains in the greenhouse and then transferred to the field after one week (2006, 2007), or first transplanted and then inoculated (2008-2010). Inoculations were conducted with either race T3 (2006) or T4 (in 2007-2010) and were achieved by spraying the plants with a bacterial suspension adjusted to $10^6$ cfu/ml in 0.025% (v/v) of Silwet L77. After completing the bacterial survey in 2006 and learning that the T4 race predominated in field trials, and because it is highly related to race T3 except it has the added ability to grow on race 3 resistant tomato hosts, we used only T4 as inoculum in all subsequent field trials. Trials occurred at the University of Florida Science Research Unit in Citra, Fla. (2006, 2007) and Gulf Coast Research and Education Center in Balm, Fla. (2007-2010). Trials were randomized complete block designs with 3-4 blocks of up to nineteen genotypes per block depending on the trial. Field plots were prepared using standard tillage practices and maintained during the trial period with standard fertilizer and pesticide regimes [39] except no bactericidal compounds were applied. Disease ratings were made at various intervals throughout the growing period. Assessments were made by estimating percent disease symptoms and defoliation caused by bacterial spot using the Horsfall-Barratt scale, where 1=0%; 2=0-3%; 3=3-6%; 4=6-12%; 5=12-25%; 6=25-50%; 7=50-75%; 8=75-87%; 9=87-93%; 10=93-97%; 11=97-100%; and 12=100% defoliation[14]. Yield determinations were made by harvesting mature-green and riper fruit from each plot. Fruit were counted and weighed for culls, small, medium, large and extra large sizes with the latter three categories comprising marketable yield, and all categories combined for total yield. Generally two harvests were made, with the exception of the Fall 2008 trial where only one harvest was made and with the exception of the Fall 2007 trial in which no fruit was harvested from the cultivar Sanibel. All field trials were carried out under Notification from the US Department of Agriculture and in accordance with an approved design protocol.

The seven trials were carried out in two locations in the Spring or Fall planting season. In one series of trials, consisting of plots at Citra (Fall 2006, Fall 2007) and Balm (Fall 2007), the extent of disease in transgenic lines was compared with ten other tomato genotypes having a range of resistance to bacterial spot. In the other series, data from five trials at the Balm Experiment Station (Fall 2007 (which had a subset of plants in common with the disease resistance series mentioned above), Spring 2008, Fall 2008, Spring 2009, and Fall 2010) were collected to examine the correlation between the extent of disease incidence and impact on yield in transgenic lines and commonly planted commercial cultivars.

Statistical Analysis

Disease ratings and yield data were evaluated with analysis of variance using PROC GLM (SAS Institute 1999) and means separated with a Duncan multiple range test (P<0.05).

Seasonal Conditions and Bs2 Impact Factor

Weather data was retrieved using the Florida Automated Weather Network (FAWN) website (fawn.ifas.ufl.edu). Typical monthly temperatures and rainfall were determined by averaging data for each month over a seven year period from 2004, the earliest year for which archived data was available, through 2010. For each month of a given year in which plants were in the field, monthly temperature and rainfall data were recorded and also expressed as a percentage of the seven-year monthly average.

TABLE 4

Field trial reports of copper effectiveness on bacterial spot disease on tomato.

| | | | Significant difference between treatment and untreated control | | | |
| --- | --- | --- | --- | --- | --- | --- |
| Year | Location | Copper treatment | Foliar Rating[a] | AUDPC[b] | Marketable Yield[c] | Ref |
| 2007 | OH | Copper hydroxide + maneb[d] | No | No | No | [1] |
| 2008 | OH | Copper hydroxide + maneb | No | No | No | [2] |
| 2008 | TN | Copper hydroxide | No | ND[e] | No | [3] |
| 2009 | OH | Copper hydroxide | Yes[f] | No | No | [4] |
| 2009 | VA | Copper hydroxide + Serenade Max[g] | No | ND | No | [5] |
| | | Copper hydroxide + QRD146[g] | No | ND | No | |

TABLE 4-continued

Field trial reports of copper effectiveness on bacterial spot disease on tomato.

| Year | Location | Copper treatment | Foliar Rating[a] | AUDPC[b] | Marketable Yield[c] | Ref |
|---|---|---|---|---|---|---|
| 2010 | FL | Copper sulfate + mancozeb[d] | No | No | No | [6] |
|  |  | Copper hydroxide | No[h] | Yes[h] | No |  |
| 2010 | FL | Copper hydroxide + mancozeb | No | No | ND | [7] |
| 2010 | FL | Copper sulfate + mancozeb | No | No | No | [8] |
| 2010 | FL | Copper sulfate + mancozeb | No | No | No | [9] |

[a]Foliar ratings were reported as Horsfall-Barratt ratings or percent diseased foliage.
[b]Area under the disease progress curve.
[c]Total of medium, large, and extra-large fruit.
[d]Maneb and mancozeb are ethylenebisdithiocarbamate (EBDC) fungicides.
[e]ND, Not determined.
[f]Foliar symptoms were lower on copper treated plots. Fruit symptoms were not.
[g]Serenade Max and QRD146 are biopesticides comprised of non-pathogenic bacterial strains, sold by AgraQuest, Davis, CA.
[h]Early season ratings showed decreased disease symptoms but later ratings were not different. Disease development, assessed by AUDPC, was significantly lower with copper treatment.
[1]. Miller SA, Mera JR, Xu X, Baysal F (2008) Evaluation of fungicides and bactericides for the control of foliar and fruit diseases of processing tomatoes, 2007. Plant Disease Management Reports 2: V037.
[2]. Miller SA, Mera JR (2009) Evaluation of fungicides and bactericides for the control of foliar and fruit diseases of processing tomatoes, 2008. Plant Disease Management Reports 3: V008.
[3]. Canaday CH (2009) Effects of cultivar, a SAR inducer, and fungicide reduction on disease and yield of staked-tomatoes, 2008. Plant Disease Management Reports 3: V053.
[4]. Miller SA, Mera JR, Baysal-Gurel F (2010) Evaluation of fungicides and bactericides for the control of foliar and fruit diseases of processing tomatoes, 2009. Plant Disease Management Reports 4: V011.
[5]. Rideout SL, Waldenmaier CM, Wimer AF, Stapleton JB (2010) Evaluation of selected fungicides for the management of bacterial spot in tomato, 2009. Plant Disease Management Reports 4: V028.
[6]. Vallad GE, Huang CH (2011) Evaluation of bacteriocides and Actigard for management of bacterial spot of tomato, Spring 2010. Plant Disease Management Reports 5: V067.
[7]. Zhang S, Mersha Z, Fu Y (2011) Field evaluation of Actigard for bacterial spot disease management on tomato in South Florida, 2010. Plant Disease Management Reports 5: V016.
[8]. Vallad GE, Huang CH (2011) Evaluation of Quintec for management of bacterial spot of tomato, Spring 2010. Plant Disease Management Reports 5: V061.
[9]. Huang CH, Vallad GE (2011) Evaluation of Actigard for management of bacterial spot of tomato, Spring 2010. Plant Disease Management Reports 5: V066.

TABLE 5

Bacterial spot disease races of tomato and occurrence of key effectors for resistance breeding.

|  | Effector occurrence[a] [1] | | | | |
|---|---|---|---|---|---|
| Race | AvrRxv | AvrXv3 | AvrXv4 | AvrBs2 | *Xanthomonas* species |
| T1[b] | + | − | − | + | *euvesicatoria* (Xcv) |
| T2 | − | − | − | + | *vesicatoria* (Xv) |
| T3 | − | + | + | + | *perforans* (Xp) |
| T4 | − | − | + | + | *perforans* (Xp) |
| T5 | − | − | − | + | *perforans* (Xp) |
| [c] | − | − | − | + | *gardneri* (Xg) |

[a]+ present or − absent in each race
[b]T indicates tomato races
[c]No T race designation

TABLE 6

Tomato and pepper lines used in field trials and race determinations.

| Variety | Type | Source | Bacterial Spot Race Resistance | Bacterial Spot Resistance Loci | Reference |
|---|---|---|---|---|---|
| VF 36 | CA large round FM | Scott | None | None |  |
| VF 36-Bs2 (homozygote) | CA large round FM | Jones/Stall | T1-5, *X. gardneri* | Bs2 | [1] |
| VF 36-Bs2 (hemizygote) | CA large round FM | Jones/Stall | T1-5, *X. gardneri* | Bs2 | [1] |
| Fla47 | FL Large round FM hybrid | Seminis | None | None |  |
| Fla91 | FL Large round FM hybrid | Seminis | None | None |  |
| Sebring | FL Large round FM hybrid | Syngenta | None | None |  |
| Sanibel | FL Large round FM hybrid | Seminis | None | None |  |
| H7998 | Hawaiian inbred | Stall | T1 | Rxv1-3 | [2, 3, 4] |
| H7981 | Hawaiian inbred | Stall | T3 | Xv3 | [5, 6] |
| PI 114490 | Indeterminate yellow cherry PI accession | D. Francis Ohio State | T1-4 | QTL | [7, 8] |
| FL216 | *L. pimpinellifolium* accession PI128216 crossed with FL7060 | Stall | T3 | Xv3 | [9] |
| VF36-Bs2 × 216 | Cross of VF 36-Bs2 (homozygote) and FL216 | Jones/Stall | T1-5, *X. gardneri* | Bs2, Xv3 |  |

TABLE 6-continued

Tomato and pepper lines used in field trials and race determinations.

| Variety | Type | Source | Bacterial Spot Race Resistance | Bacterial Spot Resistance Loci | Reference |
|---|---|---|---|---|---|
| Fla. 8000 | FL Large round FM parent line | Scott | T3 | Xv3 | [10] |
| Fla. 8044 | FL Large round FM parent line | Scott | None | None | |
| Fla. 8233 | FL Large round FM parent line, derived from PI114490 and HI7998 | Scott | T3-4 | Xv3 | [11] |
| Fla. 8517 | FL Roma breeding line | Scott | T3-4 | Xv3 | [11] |
| 3X-2-4 | FL large round FM parent line | Stall | T3-4 | Xv4 | [12] |
| Bonny Best | Indeterminate medium round | Stall | None | None | |
| ECW | Bell pepper | Stall | T1, T2, *X. gardneri* | unknown | [13] |

Abbreviations:
CA, California;
FM, fresh market;
FL, Florida;
PI, plant introduction,
QTL, quantitative trait locus conferring quantitative resistance;
Rxv1-3, Xv3, Xv4, Bs2, resistance genes detecting the effectors AvrRxv, AvrXv3, AvrXv4, and AvrBs2, respectively. See Table 5 for description of bacterial spot races and effector composition.
1. Tai TH, Dahlbeck D, Clark ET, Gajiwala P, Pasion R, et al. (1999) Expression of the Bs2 pepper gene confers resistance to bacterial spot disease in tomato. Proc Natl Acad Sci USA 96: 14153-14158.
2. Scott JW, Jones JB, Somodi GC (2001) Inheritance of resistance in tomato to race T3 of the bacterial spot pathogen. J Amer Soc Hort Sci 126: 436-441.
3. Scott JW, Stall RE, Jones JB, Somodi GC (1996) A single gene controls the hypersensitive response of Hawaii 7981 to race 3 (T3) of the bacterial spot pathogen. Rpt Tomato Genet Coop 46.
4. Wang J-F, Jones JB, Scott JW, Stall RE (1994) Several genes in *Lycopersicon esculentum* control hypersensitivity to *Xanthomonas campestris* pv. *vesicatoria*. Phytopathology 84: 702-706.
5. Jones JB, Scott JW (1986) Hypersensitive response in tomato to *Xanthomonas campestris* pv. *vesicatoria*. Plant Disease 70: 337-339.
6. Scott JW, Jones JB (1989) Inheritance of resistance to foliar bacterial spot of tomato incited by *Xanthomonas campestris* pv. *vesicatoria*. J Amer Soc Hort Sci 114: 111-114.
7. Scott JW, Francis DM, Miller SA, Somodi GC, Jones JB (2003) Tomato bacterial spot resistance derived from PI114490; Inheritance of resistance to Race T2 and relationship across three pathogen races. J Amer Soc Hort Sci 128: 698-703.
8. Scott JW, Hutton SF, Jones JB, Francis DM, Miller SA (2006) Resistance to bacterials spot race T4 and breeding for durable and broad resistance to other races. Rpt Tomato Genet Coop 56: 33-36.
9. Robbins MD, Darrigues A, Sim S-C, Masud MAT, Francis DM (2009) Characterization of hypersensitive resistance to bacterial spot Race T3 (*Xanthomonas perforans*) from tomato accession PI 128216. Phytopathology 99: 1037-1044.
10. Yang WC, Francis DM (2007) Genetics and breeding for resistance to bacterial diseases in tomato. In: Razdan MK, Mattoo AK, eds. Genetic Improvement of Solanaceous Crops. Enfield, NH, USA: Science Publishers. pp. 379-419.
11. Hutton SF, Scott JW (2010) Inheritance of resistance to bacterial spot Race T4 from three tomato breeding lines with differing resistance backgrounds. J Amer Soc Hort Sci 135: 150-158.
12. Astua-Monge G, Minsavage GV, Stall RE, Vallejos CE, Davis MJ, et al. (2000) Xv4-vrxv4: a new gene-for-gene interaction identified between *Xanthomonas campestris* pv. *vesicatoria* race T3 and wild tomato relative *Lycopersicon pennellii*. Molecular Plant-Microbe Interactions 13: 1346-1355.
13. Minsavage G, Dahlbeck D, Whalen M, Kearney B, Bonas U, et al. (1990) Gene-for-gene relationships specifying disease resistance in *Xanthomonas campestris* pv. *vesicatoria* - pepper interactions. Mol Plant Microb Interact 3: 41-47.

TABLE 7

Comparison of bacterial spot disease severity in tomato lines in Florida field trials.

| Plant Line | Fall 2006 Citra Mean[2] | Fall 2007 Citra Mean | Fall 2007 Balm[1] Mean | Overall Mean |
|---|---|---|---|---|
| VF 36-Bs2 × 216 | $1.2^E$ | $2.0^D$ | $3.6^{EF}$ | $2.3^F$ |
| VF 36-Bs2 (homo) | $1.0^E$ | $2.0^D$ | $4.0^E$ | $2.3^F$ |
| VF 36-Bs2 (hemi) | $1.0^E$ | $2.0^D$ | $4.0^E$ | $2.3^F$ |
| PI 114490 | $2.7^D$ | $4.7^C$ | $3.4^F$ | $3.6^E$ |
| Fla. 8517 | $4.0^{CD}$ | $4.5^C$ | $3.9^{EF}$ | $4.1^{DE}$ |
| HI7981 | $4.5^{BC}$ | $4.5^C$ | $5.4^D$ | $4.8^{CD}$ |
| HI7998 | $4.5^{BC}$ | $4.5^C$ | $5.6^{CD}$ | $4.9^{CD}$ |
| FL216 | $5.2^{A-C}$ | $5.2^C$ | $6.0^{BC}$ | $5.5^{BC}$ |
| Fla. 8233 | $5.0^{A-C}$ | $6.5^B$ | $5.6^{CD}$ | $5.7^B$ |
| Fla47 | $5.2^{A-C}$ | $8.0^A$ | $5.5^{CD}$ | $6.2^{AB}$ |
| Fla. 8000 | $4.0^{CD}$ | $8.0^A$ | $5.7^{B-D}$ | $6.6^A$ |
| Fla. 8044 | $6.0^{AB}$ | $7.5^A$ | $6.2^B$ | $6.6^A$ |
| VF 36 | $6.5^A$ | $7.5^A$ | $7.0^A$ | $7.0^A$ |

[1] *Alternaria* present in this trial produced bacterial spot-like disease symptoms and higher than typical scores, including on Bs2 lines.
[2] Disease severity scores were determined using the Horsfall-Barratt scale (FIG. 1). Treatment differences were determined using the Waller-Duncan T-test (p < 0.05). Mean values with identical letters were not significantly different.

TABLE 8

Comparison of disease severity and yield in transgenic and commercial tomato lines in Balm, Florida, field trials.

A. Bacterial spot disease severity

| Plant Line | Fall 2007 Mean[1,2] | Spring 2008 Mean | Fall 2008 Mean | Spring 2009 Mean | Fall 2010 Mean |
|---|---|---|---|---|---|
| VF 36-Bs2 (homo) | $4.0^D$ | $1.7^C$ | $1.5^C$ | $1.0^C$ | $1.0^D$ |

TABLE 8-continued

Comparison of disease severity and yield in transgenic and commercial tomato lines in Balm, Florida, field trials.

| | | | | | |
|---|---|---|---|---|---|
| VF 36-Bs2 (hemi) | $4.0^D$ | $1.7^C$ | $2.0^C$ | $1.0^C$ | $1.0^D$ |
| Fla91 | $5.5^C$ | $5.7^B$ | $4.0^B$ | $5.7^B$ | $3.3^C$ |
| Sanibel | $6.0^{BC}$ | $5.7^B$ | $3.7^B$ | $5.7^B$ | $3.3^C$ |
| Fla47 | $5.5^C$ | $6.5^{AB}$ | $4.0^B$ | $5.3^B$ | $3.3^C$ |
| Sebring | $6.2^B$ | $6.7^A$ | $6.0^A$ | $6.0^B$ | $4.5^B$ |
| VF 36 | $7.0^A$ | $7.2^A$ | $5.2^{AB}$ | $7.7^A$ | $5.8^A$ |

B. Yield

| | Fall 2007 | | Spring 2008 | | Fall 2008 | | Spring 2009 | | Fall 2010 | |
|---|---|---|---|---|---|---|---|---|---|---|
| Plant Line | Marketable Yield[2,3] | Total Yield | Marketable Yield | Total Yield | Marketable Yield[3] | Total Yield[3] | Marketable Yield | Total Yield | Marketable Yield | Total Yield |
| VF 36-Bs2 (homo) | $0.53^{BC}$ | $0.90^B$ | $1.12^A$ | $2.27^A$ | $0.50^A$ | $0.68^{AB}$ | $2.47^A$ | $3.29^A$ | $2.28^B$ | $3.09^{B-D}$ |
| VF 36-Bs2 (hemi) | $0.75^{AB}$ | $1.11^{AB}$ | $1.25^A$ | $2.67^A$ | $0.49^A$ | $0.67^{AB}$ | $1.99^A$ | $2.70^{A-C}$ | $2.24^B$ | $2.84^{CD}$ |
| Fla91 | $0.88^{AB}$ | $1.02^{AB}$ | $1.58^A$ | $2.31^A$ | $0.43^{AB}$ | $0.64^{A-B}$ | $2.13^A$ | $3.03^A$ | $2.11^B$ | $2.61^{CD}$ |
| Sanibel | $ND^4$ | $ND^4$ | $1.37^A$ | $2.39^A$ | $0.48^A$ | $0.86^A$ | $1.85^A$ | $2.58^{A-C}$ | $3.65^A$ | $4.46^A$ |
| Fla47 | $1.23^A$ | $1.50^A$ | $1.13^A$ | $2.28^A$ | $0.44^{AB}$ | $0.64^{A-C}$ | $1.94^A$ | $2.43^{A-C}$ | $3.21^A$ | $3.67^{A-C}$ |
| Sebring | $0.71^{AB}$ | $0.87^B$ | $1.53^A$ | $2.30^A$ | $0.28^{AB}$ | $0.43^{BC}$ | $1.79^A$ | $2.30^{BC}$ | $3.38^A$ | $4.05^{AB}$ |
| VF 36 | $0.06^C$ | $0.12^C$ | $0.45^B$ | $1.45^B$ | $0.20^B$ | $0.31^C$ | $0.95^B$ | $1.77^C$ | $1.49^B$ | $2.40^D$ |

[1]Disease severity scores were determined using the Horsfall-Barratt scale (FIG. 1). *Alternaria* present in the Fall 2007 trial produced bacterial spot-like disease symptoms and higher than typical scores, including on Bs2 lines.
[2]Treatment differences were determined using the Waller-Duncan T-test (p < 0.05). Mean values with identical letters were not significantly different.
[3]Yields are kg per plant. Marketable yield is medium, large, and extra large fruit. Total yield is all fruit including small fruit and culls. Except for the Fall 2008 trial, all trials were harvested two times and yield measurements are the total of both harvests. The Fall 2008 trial was harvested only once.
[4]Not determined.

TABLE 9

Combined field trial analysis for Balm, FL.

| Plant Line | Disease rating[2,3] | 2007-2010[1] Marketable Yield (kg)[3,4] | Total Yield (kg)[3,4] |
|---|---|---|---|
| VF 36-Bs2 (homo) | $1.9^D$ | $1.27^B$ | $1.92^B$ |
| VF 36-Bs2 (hemi) | $2.0^D$ | $1.26^B$ | $1.91^B$ |
| Fla91 | $4.9^C$ | $1.40^B$ | $1.89^B$ |
| Sanibel | $5.0^C$ | $1.80^A$ | $2.56^A$ |
| Fla47 | $5.0^C$ | $1.54^{AB}$ | $2.08^B$ |
| Sebring | $6.0^B$ | $1.49^{AB}$ | $1.94^B$ |
| VF 36 | $6.6^A$ | $0.57^C$ | $1.11^C$ |

[1]Combined analysis of 2007-2010 data presented in Table 8.
[2]Disease severity scores were determined using the Horsfall-Barratt scale (FIG. 1).
[3]Treatment differences were determined using the Waller-Duncan T-test (p < 0.05). Mean values with identical letters were not significantly different.
[4]Yields are kg per plant. Marketable yield is medium, large, and extra large fruit. Total yield is all fruit including small fruit and culls.

TABLE 10

Temperature and rainfall data for trials in Balm, FL.

A. Temperatures (degrees F.)

| | Fall 2007 | | | Spring 2008 | | Fall 2008 | | Spring 2009 | | Fall 2010 | |
|---|---|---|---|---|---|---|---|---|---|---|---|
| | Ave T[a] | T[b] | % Ave[c] | T | % Ave | T | % Ave | T | % Ave | T | % Ave |
| April | 68.93 | | | 69.66 | 101 | | | 70.75 | 103 | | |
| May | 75.37 | | | 77.07 | 102 | | | 75.80 | 101 | | |
| June | 79.12 | | | 79.48 | 100 | | | 80.62 | 102 | | |
| July | 79.98 | | | 79.74 | 100 | | | 80.71 | 101 | | |
| August | 80.34 | 81.93 | 102 | 80.67 | 100 | | | | | | |
| September | 78.80 | 79.26 | 101 | | | 80.27 | 102 | | | 78.64 | 100 |
| October | 73.72 | 76.63 | 104 | | | 73.12 | 99 | | | 71.91 | 98 |
| November | 65.99 | 66.01 | 100 | | | 62.83 | 95 | | | 65.65 | 99 |
| December | 60.61 | 66.30 | 109 | | | 64.16 | 106 | | | 50.07 | 83 |

TABLE 10-continued

Temperature and rainfall data for trials in Balm, FL.

B. Rainfall (inches)

| | Average | Fall 2007 | | Spring 2008 | | Fall 2008 | | Spring 2009 | | Fall 2010 | |
|---|---|---|---|---|---|---|---|---|---|---|---|
| | total rain for month[a] | total rain[b] | % Ave[c] | total rain | % Ave | total rain | % Ave | total rain | % Ave | total rain | % Ave |
| April | 1.67 | | | 0.03 | 2 | | | 0 | 0 | | |
| May | 2.67 | | | 2.81 | 105 | | | 6.30 | 236 | | |
| June | 7.29 | | | 5.85 | 80 | | | 4.80 | 66 | | |
| July | 8.85 | | | 8.73 | 99 | | | 4.39 | 50 | | |
| August | 7.19 | 5.78 | 80 | 7.63 | 106 | | | | | | |
| September | 5.58 | 3.95 | 71 | | | 0.64 | 11 | | | 3.42 | 61 |
| October | 2.26 | 6.42 | 284 | | | 1.40 | 62 | | | 0.01 | 0 |
| November | 1.44 | 0.02 | 1 | | | 1.49 | 103 | | | 1.24 | 86 |
| December | 1.48 | 0.94 | 64 | | | 1.36 | 92 | | | 0.50 | 34 |

[a] Average temperatures and average total rainfall for each month were determined by averaging monthly data for the seven years from 2004 to 2010. All weather data was retrieved using the Florida Automated Weather Network (FAWN) weather archive web site.
[b] Data are reported in each trial period only for months in which trial plants were in the field. Monthly temperature (T) is the average for that month in the given year, and total rain is the total precipitation for the month.
[c] '% Ave' is the monthly temperature or total rain calculated as a percent of the average values for that month.

REFERENCES

For Example 1 and Prior Numerical Citations in the Specification

1. Pohronezny K, Volin R B (1983) Effect of bacterial spot on yield and quality of fresh market tomatoes. HortScience 18: 69-70.
2. Glades Crop Care website (1999) Crop profiles for south Florida tomatoes. Available: http://wwwgladescropcare-com/CP_tomatoes.pdf. Accessed 2012 Jul. 5.
3. Stall R E, Thayer P L (1962) Streptomycin resistance of the bacterial spot pathogen and control with streptomycin. Plant Disease Reporter 46: 389-392.
4. Thayer P L, Stall R E (1962) A survey of Xanthomonas vesicatoria resistance to streptomycin. Florida Agricultural Experiment Station Journal 1523: 163-165.
5. Marco G M, Stall R E (1983) Control of bacterial spot of pepper initiated by strains of Xanthomonas campestris pv. vesicatoria that differ in sensitivity to copper. Plant Disease 67: 779-781. doi: 10.1094/PD-67-779.
6. Huang C H, Vallad G E (2011) Evaluation of Actigard for management of bacterial spot of tomato, Spring 2010. Plant Disease Management Reports 5: V066.
7. Vallad G E, Huang C H (2011) Evaluation of bacteriocides and Actigard for management of bacterial spot of tomato, Spring 2010. Plant Disease Management Reports 5: V067.
8. Vallad G E, Huang C H (2011) Evaluation of Quintec for management of bacterial spot of tomato, Spring 2010. Plant Disease Management Reports 5: V061.
9. Zhang S, Mersha Z, Fu Y (2011) Field evaluation of Actigard for bacterial spot disease management on tomato in South Florida, 2010. Plant Disease Management Reports 5: V016.
10. Biffen R (1905) Mendel's laws of inheritance and wheat breeding. J Agric Sci 1: 4-48. doi: 10.1017/S0021859600000496.
11. Chisholm S T, Coaker G, Day B, Staskawicz B J (2006) Host-microbe interactions: shaping the evolution of the plant immune response. Cell 124: 803-814. doi: 10.1016/j.cell.2006.02.008.
12. Kearney B, Staskawicz B J (1990) Widespread distribution and fitness contribution of Xanthomonas campestris avirulence gene avrBs2. Nature 346: 385-386. doi: 10.1038/346385a0.
13. Tai T H, Dahlbeck D, Clark E T, Gajiwala P, Pasion R, et al. (1999) Expression of the Bs2 pepper gene confers resistance to bacterial spot disease in tomato. Proc Natl Acad Sci USA 96: 14153-14158. doi: 10.1073/pnas.96.24.14153.
14. Horsfall J, Barratt R (1945) An improved grading system for measuring plant disease. Phytopahtology 36: 655.
15. Green J, Wang D, Lilley C, Urwin P, Atkinson H (2012) Transgenic potatoes for potato cyst nematode control can replace pesticide use without impact on soil quality. PLoS ONE 7: e30973. doi: 10.1371/journal.pone.0030973.
16. Vishnevetsky J, White Jr T, Palmateer A, Flaishman M, Cohen Y, et al. (2011) Improved tolerance toward fungal diseases in transgenic Cavendish banana (Musa spp. AAA group) cv. Grand Nain. Transgenic Res 20: 61-72. doi: 10.1007/s11248-010-9392-7.
17. Krens F, Schaart J, Groenwold R, Walraven A, Hesselink T, et al. (2011) Performance and long-term stability of the barley hordothionin gene in multiple apple lines. Transgenic Res 20: 1113-1123. doi: 10.1007/s11248-011-9484-z.
18. Bravo-Almonacid F, Rudoy V, Welin B, Segretin M, Bedogni M, et al. (2011) Field testing, gene flow assessment and pre-commercial studies on transgenic Solanum tuberosum spp. tuberosum (cv. Spunt) selected for PVY resistance in Argentina. Transgenic Res doi:10.1007/s11248-011-9584-9.
19. Halterman D, Kramer L, Wielgus S, Jiang J (2008) Performance of transgenic potato containing the late blight resistance gene RB. Plant Disease 92: 339-343. doi: 10.1094/PDIS-92-3-0339.
20. Sasu M, Ferrari M, Du D, Winsor J, Stephenson A (2009) Indirect costs of a nontarget pathogen mitigate the direct benefits of a virus-resistant transgene in wild Cucurbita. Proc Natl Acad Sci USA doi:10.1073/pnas.0905106106.
21. Ferreira S, Pitz K, Manshardt R, Zee F, Fitch M (2002) Virus coat protein transgenic papaya provides practical control of papaya ringspot virus in Hawaii. Plant Disease 86: 101-105. doi: 10.1094/PDIS.2002.86.2.101.
22. Rowell B, Jones R, Nesmith W, Satanek A, Snyder J (2001) Bacterial spot resistance, yield, and quality of bell and specialty peppers. HortTechnology 11: 648-657.
23. Rowell B, Jones R, Nesmith W, Snyder J (1999) Comparison of resistant cultivars for management of bacterial spot in peppers. HortTechnology 9: 641-650.

24. Fan J, Zhenli H, Ma L Q, Stoffella P J (2011) Accumulation and availability of copper in citrus grove soils as affected by fungicide application. J Soils Sediments 11: 639-648. doi: 10.1007/s11368-011-0349-0.

25. Toor G S, Chahal M K, Santos B M (2010) Wastewater characterization in Florida tomato packinghouses. Proc Florida Tomato Institute. 8-9.

26. Fuchs M, Gonsalves D (2007) Safety of virus-resistant transgenic plants two decades after their introduction: Lessons from realistic field risk assessment studies. Annu Rev Phytopathol 45: 173-202. doi: 10.1146/annurev.phyto.45.062806.094434.

27. Li J, Ding J, Zhang W, Zhang Y, Tang P, et al. (2010) Unique evolutionary pattern of numbers of gramineous NBS-LRR genes. Mol Genet Genomics 283: 427-438. doi: 10.1007/s00438-010-0527-6.

28. Zhang M, Wu Y-H, Lee M-K, Liu Y-H, Rong Y, et al. (2010) Numbers of genes in the NBS and RLK families vary by more than four-fold within a plant species and are regulated by multiple factors. Nucleic Acids Research 38: 6513-6525. doi: 10.1093/nar/gkq524.

29. Groenewegen C, King G, George B F (1994) Natural cross pollination in California commercial tomato fields. HortScience 29: 1088.

30. Swords K M, Dahlbeck D, Kearney B, Roy M, Staskawicz B J (1996) Spontaneous and induced mutations in a single open reading frame alter both virulence and avirulence in *Xanthomonas campestris* pv. *vesicatoria* avrBs2. Journal of Bacteriology 178: 4661-4669.

31. Wichmann G, Ritchie D, Kousik C S, Bergelson J (2005) Reduced genetic variation occurs among genes of the highly clonal plant pathogen *Xanthomonas axonopodis* pv. *vesicatoria*, including the effector gene avrBs2. Applied and Environmental Microbiology 71: 2418-2432. doi: 10.1128/AEM.71.5.2418-2432.2005.

32. Zhao B, Dahlbeck D, Krasileva K V, Fong R W, Staskawicz B J (2011) Computational and biochemical analysis of the *Xanthomonas* effector AvrBs2 and its role in the modulation of *Xanthomonas* type three effector delivery. PLoS Pathog 7: e1002408. doi: 10.1371/journal.ppat.1002408.

33. Astua-Monge G, Minsavage G V, Stall R E, Vallejos C E, Davis M J, et al. (2000) Xv4-vrxv4: a new gene-for-gene interaction identified between *Xanthomonas campestris* pv. *vesicatoria* race T3 and wild tomato relative *Lycopersicon pennellii*. Molecular Plant-Microbe Interactions 13: 1346-1355. doi: 10.1094/MPMI.2000.13.12.1346.

34. Robbins M D, Darrigues A, Sim S-C, Masud M A T, Francis D M (2009) Characterization of hypersensitive resistance to bacterial spot Race T3 (*Xanthomonas perforans*) from tomato accession PI 128216. Phytopathology 99: 1037-1044. doi: 10.1094/PHYTO-99-9-1037.

35. Scott J W, Jones J B, Somodi G C (2001) Inheritance of resistance in tomato to race T3 of the bacterial spot pathogen. J Amer Soc Hort Sci 126: 436-441.

36. Scott J W, Stall R E, Jones J B, Somodi G C (1996) A single gene controls the hypersensitive response of Hawaii 7981 to race 3 (T3) of the bacterial spot pathogen. Rpt Tomato Genet Coop 46.

37. Wang J-F, Jones J B, Scott J W, Stall R E (1994) Several genes in *Lycopersicon esculentum* control hypersensitivity to *Xanthomonas campestris* pv. *vesicatoria*. Phytopathology 84: 702-706.

38. Stall R, Loschke D, Jones J (1986) Linkage of copper resistance and avirulence loci on a self-transmissible plasmid in *Xanthomonas campestris* pv. *vesicatoria*. Phytopathology 76: 240-243. doi: 10.1094/Phyto-76-240.

39. Olson S M, Stall W M, Momol M T, Webb S E, Taylor T G, et al. (2007) Tomato production in Florida. In: Simonne SMOaE, editor. Vegetable Production Handbook for Florida: IFAS Publ., Univ. of Florida. 409-428.

Example 2

The Pepper Bs2 Gene Confers Effective Field Resistance to Bacterial Leaf Spot and Yield Enhancement in Florida Tomatoes Bacterial leaf spot disease, caused by a disease complex of *Xanthomonas* species, continues to be a major cause of crop loss for fresh market tomatoes in Florida and is a serious disease of tomato and pepper in tropical and subtropical regions world-wide. Standard chemical control with copper-based fungicides has led to the appearance of resistant strains, and efficacious, cost-effective crop protection compounds are lacking. In addition, strains have changed over time, making breeding for resistance to bacterial spot a challenging, moving target (Stall et al., 2009). Currently no commercial cultivars confer adequate protection against the disease.

We have investigated a transgenic approach to disease resistance in tomato based on the resistance gene, Bs2, from pepper. Bs2 is of particular interest as a resistance gene because it comes from a close relative of tomato and is a member of the most common disease resistant gene family, known as NB-LRRs, for nucleotide-binding, leucine-rich repeat gene (Eitas and Dangl, 2010). These features mean that the trait and its mode of action are commonly found in *Solanaceous* plants, which may improve both the likelihood of functionality and the acceptability of the trait to consumers. Yet in the interest of durable disease resistance, the most important feature of Bs2 is that it recognizes AvrBs2, an effector that is highly conserved across a range of *Xanthomonas* species, (Kearney and Staskawicz, 1990). Introduction of the Bs2 cDNA into a California tomato cultivar conferred resistance in greenhouse tests (Tai et al., 1999) and field trials (Horvath, et al., 2011) with a highly significant level of disease reduction and increase in fruit yields relative to controls. However, the VF36 background is not adapted to Florida growing conditions, and it was not known if the introduction of Bs2 into Florida cultivars would produce similar results. In the current study, we report on results from three field trials designed to examine the impact of Bs2 on Florida tomato production.

All Bs2 transgenic lines and/or tomato plants described in Example 2 comprise transgenic event Bs2-X5, which comprises the Bs2 gene.

Materials and Methods

The California cultivar 'VF36' was previously transformed with the pepper Bs2 gene under the control of the cauliflower mosaic virus 35S promoter to generate the transgenic line 'VF36-Bs2' (Tai et al., 1999). VF36-Bs2 plants were crossed with Florida parent lines Fla. 8000 or Fla. 8111B to create the transgenic versions, Fla. 8000-Bs2 and Fla. 8111B-Bs2. In these lines, the transgene cassette consists of the Bs2 gene driven by the CaMV 35S promoter and the selectable marker gene, nptII. The Fla. 8000-Bs2 and Fla. 8011b-Bs2 lines were used to make the high performing hybrid, Fla. 8314. Hybrids were also made with other non-transgenic parent lines carrying additional disease resistance loci including Xv4 (also known as RXopJ, for bacterial spot), Fr1 (*Fusarium* crown rot), *fusarium* wilt race 3, and Ty-1 (tomato yellow leaf curl virus) (Berry and Oakes, 1987; Scott and Jones, 1995; Verlaan et al., 2013. We also made a second set of FL8000-Bs2 lines by direct transformation of Fla. 8000 with a Bs2 gene construct under the expression of the tomato RbcS2 gene promoter (Sugita et al., 1987). In these lines, nptII was segregated away from Bs2 to produce plants containing introduced sequences made up of only tomato and pepper genetic elements. We focused on breeding line Fla. 8000 as a good background for introducing the Bs2 gene, because it is heat-tolerant and has conventional resistance to *X. perforans* race T3 as support to Bs2. Fla. 8000 is a parent in Fla. 8314, a hybrid that has consistently demonstrated good marketable yields in previous testing (Scott et al, 2011). Various lines were field tested in replicated trials in fall 2011, spring 2012, and/or fall 2012, at the University of Florida Gulf Coast Research and Education Center located in Balm, Fla. Lines were compared with the widely used commercial cultivars 'Florida 47' 'Florida 91', and 'Sanibel' in randomized complete block designs with 3 replications of each genotype and 7-10 plants per replicate. Except for the 2011 fall trial in which infection occurred by endemic *X. perforans*, plants were typically inoculated approximately 3 weeks after transplanting with a $10^8$ cfu/ml suspension of a race T4 strain of *Xanthomonas perforans*, using a back-pack sprayer. Plots were rated for bacterial spot severity of one or more times between 3-8 weeks following inoculation by assessing the percent defoliation according to the Horsfall-Barratt scale where, 1=0%; 2=0-3%; 3=3-6%; 4=6-12%; 5=12-25%; 6=25-50%; 7=50-75%; 8=75-87%; 9=87-93%; 10=93-97%; 11=97-100%; 12=100% defoliation. For TYLCV, plants were rated on a 0-4 scale where 4=severe symptoms and stunting; 3=severe symptoms; 2=moderate symptoms; 1=slight symptoms; and 0=no symptoms (Griffiths and Scott, 2001). Fruits were harvested at the breaker stage and beyond two or more times per season at one week intervals. Fruit were separated into marketable and unmarketable categories, and marketable fruit was sized according to USDA standards. Analysis of variance and Duncan's mean separation procedures were conducted for all variables measured using SAS (SAS Institute, Cary, N.C.).

Results and Discussion

Three trials were carried out in 2011 and 2012 to examine the impact of the pepper Bs2 gene in tomato parent lines and hybrids adapted for the Florida tomato market, where bacterial spot disease is a chronic and serious production constraint.

In the fall 2011 trial, a yield boost was observed in both Fla. 8000 and 8314 when the Bs2 gene was present, with a more than two-fold increase in the total and extra-large fruit yield of these lines compared to their respective non-Bs2 counterparts and of Fla. 8314-Bs2 compared to Florida 47 (data not shown).

In 2012, a trial was planted in late spring and went through heavy rains in early June, bringing in bacterial spot when the vines were nearly full-sized. The 3$^{rd}$ harvest came right after Tropical Storm Debby. A high cull rate was observed due to fruit cracking and checking, and marketable yields were lower than in other spring trials. Both Fla. 8000 and Fla. 8314 with Bs2 had significantly greater total yields than their respective non-Bs2 counterparts (data not shown). A lower cull rate was also observed in these lines, possibly due to better leaf cover of the fruit. 8314-Bs2 had over twice the yield of extra-large marketable fruit than both untransformed 8314 and Florida 47.

A 2012 fall trial included an expanded set of 14 additional hybrid lines containing Bs2, which were generated by crossing 14 different parent lines with Fla. 8000-Bs2 or Fla. 8111B-Bs2. All parent lines and hybrids without the Bs2 gene were susceptible to *X. perforans* with bacterial leaf spot symptoms ranging from 5.4-7.3 on the Horsfall-Baratt scale, whereas all entries carrying the Bs2 gene had essentially no observable disease and Horsfall-Barratt scores of 1-1.3. Disease severity scores are shown in Table 11 for entries selected for yield analysis. In addition to bacterial spot symptoms, lines were rated for severity of TYLCV symptoms to assess the impact of the Ty1 locus which was present in some lines. As shown in Table 11, several lines were found to be free of both observable bacterial spot and TYLCV symptoms. The further development of such lines could provide highly useful resistance against two of the most common and destructive diseases to Florida fresh market tomato production, while enabling a reduction in the use of crop protection chemicals currently used to control these diseases.

As in the two previous trials, yields were again increased in lines carrying the Bs2 gene. As shown in Table 12, comparisons of closely related lines differing in the presence or absence of Bs2 or Bs2 and Ty1 showed increases in total marketable yields between 1.7 and 2.3 fold and in the marketable yields of extra-large fruit between 2.1 and 4.2 fold. TYLCV severity was negatively correlated with marketable weight. ($R^2$=–0.17*) and extra large weight. ($R^2$=–0.13) and positively correlated with culls ($R^2$=0.32***). The best overall extra-large and total yields were from the transgenic hybrid 8455, carrying both Bs2 and Ty1. Building on our earlier data in tomato germplasm not adapted to Florida growing conditions (Horvath et al., 2011), these results demonstrate that Bs2 can have a positive impact in commercial tomato hybrids bred for Florida fresh market production.

Literature Cited

In Example 2

Berry, S. Z. and G. L. Oakes. 1987. Inheritance of resistance to *fusarium* crown and root rot in tomato. HortScience. 22:110-111.

Eitas, T. K. and J. L. Dangl. 2010. NB-LRR proteins: pairs, pieces, perception, partners, and pathways. Curr. Op. Plant Biol. 13:472-477.

Griffiths, P. D. and J. W. Scott. 2001. Inheritance and linkage of tomato mottle virus resistance genes derived from *Lycopersicon chilense* accession LA 1932. J. Amer. Soc. Hort. Sci. 126(4):462-467.

Horvath, D. M., Stall, R. E., Jones, J. B., Pauly, M. H., Vallad, G. E., Dahlbeck, D., Staskawicz, B. J., and J. W. Scott. 2011. Transgenic resistance confers effective filed level control of bacterial disease in tomato. PLoS ONE http://www.plosone.org/article/info %3Adoi %2F10.1371%2Fjournal.pone.0042036

Kearney, B. and B. J. Staskawicz. 1990. Widespread distribution and fitness contribution of *Xanthomonas campestris* avirulence gene avrBs2. Nature 346:385-386.

Scott, J. W. and J. P. Jones. 1995. Fla. 7547 and Fla. 7481 tomato breeding lines resistant to *Fusarium oxysporum* f. sp. *lycopersici* races 1, 2, and 3. HortScience 30(3):645-646.

Scott, J. W., G. E. Vallad, R. E. Stall, J. B. Jones, D. Dahlbeck, and B. J. Staskawicz. 2011. Bacterial spot race T4 resistance and yield enhancement in tomatoes conferred by the pepper Bs2 gene in Florida field trials. Acta Horticulturae 914:437-440.

Stall, R. E., Jones, J. B., and G. V. Minsavage. 2009. Durability of resistance in tomato and pepper to Xanthomonads causing bacterial spot. Annu. Rev. Phytopathol. 47:265-284.

Sugita, M. Manzara, T., Pichersky, E., Cashmore, A., and W. Gruissem. 1987. Genomic organization, sequence analysis and expression of all five genes encoding the small subunit of ribulose-1,5-bisphophate carboxylase/oxygenase from tomato. Mol. Gen. Genet 209:247-256.

Tai, T. H., Dahlbeck, D., Clark, E. T., Gajiwala, P., Pasion, R., Whalen, M. C., Stall, R. E., and B. J. Staskawicz. 1999. Expression of the Bs2 pepper gene confers resistance to bacterial spot disease in tomato. PNAS 96:14153-14158.

Verlaan, M. G., Hutton, S. F., Ibrahem, R. M., Kormelink, R., Visser, R. G. F., Scott, J. W., Edwards, J. E., and Y. Bai. 2013. The Tomato Yellow Leaf Curl Virus Resistance Genes Ty-1 and Ty-3 Are Allelic and Code for DFDGD-Class RNA-Dependent RNA Polymerases. PloS Genetics http://www.plosgenetics.org/article/info doi/10.1371/journal.pgen.1003399

TABLE 11

Results of Bs2 trial in Balm, FL, Fall, 2012.

| Entry | Marketable yield (25 lb. box/acre)[x] Total | Extra-large | Fruit size (g) | Culls (% by wt.) | BLS rating[y] | TY severity[z] |
|---|---|---|---|---|---|---|
| 8455 Bs2, Ty1 | 2780 a | 2207 a | 204 a-c | 11 e | 1 d | 0 d |
| 8111B × 7781 Bs2, Ty1 Frl | 2737 a | 1860 ab | 208 a-c | 14 de | 1 d | 0 d |
| 8314 Bs2 | 2508 ab | 1933 ab | 195 b-e | 15 de | 1 d | 0.8 ab |
| 8735 × 8000 Bs2 | 2505 ab | 1836 ab | 184 c-e | 15 de | 1 d | 0.9 ab |
| 8000 Bs2 | 2476 ab | 1654 b | 177 d-f | 24 b-e | 1 d | 0.6 bc |
| 8726 Bs2, Ty1, I-3 | 2424 ab | 2025 ab | 214 ab | 17 c-e | 1 d | 0 d |
| 8476 × 8111B Bs2 | 1867 bc | 1431 c | 199 a-e | 13 de | 1 d | 0.8 ab |
| 8314 | 1434 cd | 920 de | 175 ef | 34 ab | 6.1 bc | 0.7 a-c |
| 8000 | 1300 cd | 398 f | 142 f | 28 b-d | 6.7 ab | 0.4 cd |
| 8455 | 1202 cd | 953 d | 202 a-c | 36 a | 5.4 c | 0.6 a-c |
| Sanibel | 1129 d | 904 de | 203 a-c | 39 a | 6.3 b | 0.4 cd |
| 8726 | 1089 d | 926 de | 220 a | 31 a-d | 6.5 b | 1 a |
| Florida 91 | 1056 d | 904 de | 223 a | 34 ab | 6.0 bc | 0.7 a-c |
| Florida 47 | 934 d | 810 ef | 200 a-d | 42 a | 6.0 bc | 0.8 ab |

[x]Mean separation in columns by Duncan's multiple range test at P ≤ 0.05.
[y]Horsfall-Barratt scale, higher number means more disease.
[z]Rated by plant on a 0-4 scale, higher number means more disease.

TABLE 12

Impact of Bs2 on the marketable yields of tomato lines in the Fall 2012 GCREC field trial.

| Entry | Geno-type | Marketable yield (25 lb. box/acre)[y] Total | Fold increase | Extra-large | Fold increase |
|---|---|---|---|---|---|
| 8000 | −Bs2 | 1300 cd | | 398 f | |
|  | +Bs2 | 2476 ab | 1.9 | 1654 b | 4.2 |
| 8314 | −Bs2 | 1434 cd | | 920 de | |
|  | +Bs2 | 2508 ab | 1.7 | 1933 ab | 2.1 |
| 8455 | −Bs2 | 1202 cd | | 953 d | |
|  | +Bs2 +Ty1 | 2780 a | 2.3 | 2207 a | 2.3 |
| 8726 | −Bs2 | 1089 d | | 926 de | |
|  | +Bs2 +Ty1, I-3 | 2424 ab | 2.2 | 2025 ab | 2.2 |

[y]Yield data and mean separation from Table 11.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

All references cited herein are hereby expressly incorporated herein by reference.

That which is claimed:

1. A tomato plant or seed comprising transgenic event Bs2-X5, a sample of tomato seed comprising transgenic event Bs2-X5 having been deposited under American Type Culture Collection (ATCC) Patent Deposit No. PTA-121404, wherein transgenic event Bs2-X5 comprises the insertion of a transgene into the genome of a tomato plant at a site immediately adjacent to the nucleotide sequence set forth in SEQ ID NO: 1 and wherein the transgene comprises SEQ ID NO: 42.

2. The plant or seed of claim 1, which is an inbred plant or seed.

3. The plant or seed of claim 1, which is a hybrid plant or seed.

4. A plant part of the plant of claim 1, wherein the plant part comprises transgenic event Bs2-X5.

5. The plant part of claim 4, wherein the part is selected from the group consisting of a leaf, a stem, a root, a scion, a rootstock, an ovule, pollen, a fruit, and a cell.

6. A tissue culture of regenerable cells of the plant of claim 1, wherein the tissue culture comprises transgenic event Bs2-X5.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A tomato plant regenerated from the tissue culture of claim 7, wherein the regenerated plant comprises transgenic event Bs2-X5, a sample of tomato seed comprising transgenic event Bs2-X5 having been deposited under ATCC Patent Deposit No. PTA-121404.

9. A method of vegetatively propagating the plant of claim 1 comprising the steps of:
(a) collecting tissue capable of being propagated from the plant according to claim 1;
(b) cultivating said tissue to obtain proliferated shoots; and
(c) rooting said proliferated shoots to obtain rooted plantlets.

10. The method of claim 9, further comprising growing at least a first plant from said rooted plantlets.

11. A method of introducing transgenic event Bs2-X5 into a tomato plant, the method comprising:
(a) crossing a first tomato plant comprising transgenic event Bs2-X5 with a second tomato plant lacking transgenic event Bs2-X5, a sample of seed comprising transgenic event Bs2-X5 having been deposited under ATCC Patent Deposit No. PTA-121404, wherein said tomato plant comprising transgenic event Bs2-X5 is homozygous or hemizygous for transgenic event Bs2-X5, wherein transgenic event Bs2-X5 comprises the insertion of a transgene into the genome of a tomato plant at a site immediately adjacent to the nucleotide sequence set forth in SEQ ID NO: 1 and wherein the transgene comprises SEQ ID NO: 42; and
(b) allowing seed to form, wherein at least one seed comprises transgenic event Bs2-X5.

12. A tomato plant produced by the method of claim 11, wherein the tomato plant that is produced comprises transgenic event Bs2-X5.

13. A method of producing a tomato seed comprising transgenic event Bs2-X5, the method comprising crossing the plant of claim 1 with itself or a second tomato plant and allowing seed to form, wherein at least one seed comprises transgenic event Bs2-X5.

14. A tomato seed produced by the method of claim 13, said seed comprising transgenic event Bs2-X5.

15. A method of producing a tomato fruit comprising:
(a) obtaining the plant according to claim 1, wherein the plant has been cultivated to maturity; and
(b) collecting a tomato fruit from the plant.

16. A method for increasing tomato fruit production in areas where bacterial spot disease is known to occur, the method comprising:
(a) growing tomato plants under conditions favorable for the development of bacterial spot disease, wherein said tomato plants comprise transgenic event Bs2-X5, a sample of tomato seed comprising transgenic event Bs2-X5 having been deposited at the ATCC under ATCC Patent Deposit No. PTA-121404, wherein transgenic event Bs2-X5 comprises the insertion of a transgene into the genome of a tomato plant at a site immediately adjacent to the nucleotide sequence set forth in SEQ ID NO: 1 and wherein the transgene comprises SEQ ID NO: 42; and
(b) harvesting tomato fruit from the tomato plants;
wherein the yield of tomato fruit is increased relative to the yield of tomato fruit from a control tomato plant lacking transgenic event Bs2-X5.

17. The method of claim 16, wherein the tomato plants comprising transgenic event Bs2-X5 comprise enhanced resistance to bacterial spot disease relative to the control tomato plant lacking transgenic event Bs2-X5.

* * * * *

SEQUENCE LISTING

<160> NUMBER OF SEQ ID NOS: 44

<210> SEQ ID NO 1
<211> LENGTH: 113
<212> TYPE: DNA
<213> ORGANISM: Solanum lycopersicum

<400> SEQUENCE: 1

```
caagtgcaac acaaattagg acaataatat gaattgaaga ctaaaaagta aaataataa      60 ctaatagtta aaattacaat cgaattgata accctataat ttattttata aaa           113
```

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2

```
ctaatatatg acctgtgcgt gaga                                           24
```

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3

```
gcaaatttct ggaggtacat cga                                            23
```

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4

```
caaagtcttg gagctgagac a                                              21
```

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5

```
tgtgtgtata tctgcaaact ca                                             22
```

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6

```
gttctggaaa gccacaaatg aca                                            23
```

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7

```
cacccattga gtttgcagat a                                              21
```

<210> SEQ ID NO 8
<211> LENGTH: 27

<212> TYPE: DNA
<213> ORGANISM: Artificial Sequence
<220> FEATURE:
<223> OTHER INFORMATION: Primer

<400> SEQUENCE: 8
atgttcttct gaatcagaat cactctc                                    27

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
aggcggtcga aggtgccgat a                                          21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
atcggggatc atccgggtct gt                                         22

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gcaaacttga ttctgtcgct actgat                                     26

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gtctcaatag ccctttggtc ttc                                        23

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ccttttaaat atccgattat tc                                         22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cgatagccgc gctgcctcgt                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tctcggcagg agcaaggtga                                               20

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ctgccggtcg gggagctgtt ggct                                          24

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
tacgatgaga caaccagt                                                 18

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcactggccg tcgttttaca                                               20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tcaccttgct cctgccgaga                                               20

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
tatccgatta ttctaataaa cgct                                          24

<210> SEQ ID NO 21
<211> LENGTH: 20
<212> TYPE: DNA
<213> ORGANISM: Artificial Sequence

```
<220> FEATURE:
<223> OTHER INFORMATION: Primer

<400> SEQUENCE: 21
caatctgatc atgagcggag                                               20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
tcgtttcccg ccttcagtt                                                19

<210> SEQ ID NO 23
<211> LENGTH: 17
<212> TYPE: DNA
<213> ORGANISM: Artificial Sequence
<220> FEATURE:
<223> OTHER INFORMATION: Primer

<400> SEQUENCE: 23
ataacacatt gcggacg                                                  17

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
taagttgtct aagcgtca                                                 18

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
ccaatatatc ctgtcaaaca ctga                                          24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
acctgcgtgc aatccatctt gttc                                          24

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
gaattaaggg agtcacgtta tg                                            22
```

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
actgaaggcg ggaaacgaca atct                                          24

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
actatcagtg tttgacagga                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cctaagagaa aagagcgttt                                               20

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
aggagcgggc gccattcagg ct                                            22

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gagcccccga tttagagctt ga                                            22

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
ggcaatcagc tgttgcccgt ctca                                          24

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
atcctgccac cagccagcca aca                                                    23

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
gccgatttcg gaaccaccat caaaca                                                 26

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
aattgcattg aggaaggtga tgtccta                                                27

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ttcatccacc acaagtcgat tcggcgac                                               28

<210> SEQ ID NO 38
<211> LENGTH: 31
<212> TYPE: DNA
<213> ORGANISM: Artificial Sequence
<220> FEATURE:
<223> OTHER INFORMATION: Primer

<400> SEQUENCE: 38
tgtatgcaaa acaaattata caattgcagc g                                           31

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
actcctaggt atatgccggt cacatt                                                 26

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
cgaggggaat ttatggaacg tca                                                    23

<210> SEQ ID NO 41

-continued

```
<211> LENGTH: 290
<212> TYPE: DNA
<213> ORGANISM: Solanum lycopersicum
<220> FEATURE:
<221> NAME/KEY: misc_feature
<222> LOCATION: (1)..(290)
<223> OTHER INFORMATION: LB tomato flanking sequence (63048321-63048610)

<400> SEQUENCE: 41 agtcctttg tttttccaaa ctaacctgca aatagtcggt ttgtgttatt ggtttgtttt      60
atcggttttt aattataaaa ataaatattt gaattgaata aattattatt aaatacaagt    120
gcaacacaaa ttaggacaat aatatgaatt gaagactaaa aagtaaaaat aataactaat    180
agttaaaatt acaatcgaat tgataaccct ataatttatt ttataaaatc attaaatacc   240
cattcatcaa ataatcataa actaataata ttttttaat ttaatttatt                 290

<210> SEQ ID NO 42
<211> LENGTH: 3434
<212> TYPE: DNA
<213> ORGANISM: Artificial Sequence
<220> FEATURE:
<223> OTHER INFORMATION: CaMV 35S promoter::Bs2 coding sequence
      construct

<400> SEQUENCE: 42
cttcgtcaac atggtggagc acgacacact tgtctactcc aaaaatatca aagatacagt      60
ctcagaagac caaagggcaa ttgagacttt tcaacaaagg gtaatatccg gaaacctcct    120
cggattccat tgcccagcta tctgtcactt tattgtgaag atagtggaaa aggaaggtgg    180
ctcctacaaa tgccatcatt gcgataaagg aaaggccatc gttgaagatg cctctgccga    240
cagtggtccc aaagatggac ccccacccac gaggagcatc gtggaaaaag aagacgttcc    300
aaccacgtct tcaaagcaag tggattgatg tgatatctcc actgacgtaa gggatgacgc    360
acaatcccac tatccttcgc aagacccttc ctctatataa ggaagttcat ttcatttgga    420
gagaacacgg gggactctag atggctcatg caagtgtggc ttctcttatg agaacaatag    480
aatctctctt gacattcaat tcgccgatgc aatctctatc ctgtgatcac agagaagaac    540
tttgcgctct tcgtgaaaaa gttagttccc tggaagtatt tgtcaagaac tttgagaaaa    600
acaatgtttt tggggaaatg acggattttg aagtagaggt aagagaagtt gcaagtgctg    660
ctgaatacac aattcaactg agactaacag gaactgtact gggagaaaat aaaagccaga    720 aaaaaaggc gcgtcgaagg tttcgtcaaa gcctgcaaca agtagcagag gacatggatc    780
atatctggaa agagtcgaca aagatccaag ataaaggaaa acaagtatca aaggaatcat    840
tggttcatga tttttcaagt tcaacaaacg atattttgaa ggttaagaac aatatggttg    900
gacgtgatga tcaaaggaaa cagttgttag aagatctgac tagaagctac tctggggaac    960
ccaaagtcat cccgattgtc gggatgggag cataggtaa acaaccttta gcaaaagaag   1020
tttacaatga tgaatcaatt ctatgccgtt ttgatgttca tgcctgggct accatatctc   1080
aacagcacaa caaaaggaa attttgctgg gccttctgca ttccacaatc aaaatggatg   1140
acagggttaa gatgattggt gaagcagagc tagcagacat gttacagaaa agtttaaaga   1200
gaaagaggta cttaattgtc ttggatgata tctggagttg tgaagtgtgg gatggcgtga   1260
gacgatgctt tccaactgaa gacaatgcag ggagtcgaat actgttgact acccgtaatg   1320
atgaagtagc ttgttatgct ggtgtagaga atttttctt gcggatgagc ttcatggatc   1380
aagatgagag ttggagtctt ttcaaaagtg cagcatttc aagtgaagca ttaccatatg   1440
```

| | |
|---|---|
| agttcgagac tgttggaaag caaatcgcag atgaatgtca cgggttacca ctaactattg | 1500 |
| tcgtggttgc agggcttctc aaatctaaaa ggacaataga agattggaaa actgttgcta | 1560 |
| aagatgtcaa gtcattcgtc acaaatgatc ctgatgaacg atgttcacgt gtgcttgggt | 1620 |
| tgagttacga tcacttgaca agcgatctaa aaacatgtct tctgcatttc ggaatttttc | 1680 |
| cagaagacag tgatattcca gtgaagaatt tgatgagatc atggatggct gagggttcc | 1740 |
| tgaagttgga aaatgatttg gaaggagagg ttgagaagtg tttgcaagag cttgtcgata | 1800 |
| gatgtctagt cctcgtcagc aagagaagtc gagatggaac aaaaattaga tcatgtaagg | 1860 |
| ttcatgatct aatatatgac ctgtgcgtga gagaagttca agggagaac attttatca | 1920 |
| tgaacgacat tgttcttgac gtatcatatc cagaatgttc atatctctgt atgtataaaa | 1980 |
| tgcagccctt taagcgcgtg actggtgatg aaattaatta ttgtccctat ggtctttata | 2040 |
| gggctcttct tacccctgta aatcgtcagt tgagagatca tgacaacaac aatcttttga | 2100 |
| aacgaaccca ttctgttttc tcttttcatc ttgagccttt atattatgtt ctcaaatcag | 2160 |
| aggttgttca tttcaaatta ctcaaagtct tggagctgag acacagacag attgatggtt | 2220 |
| tccctcgaga gatactaagc ctcatctggt tgaggtacct atcattgttc agctatggga | 2280 |
| atttcgatgt acctccagaa atttgcaggt tatggaatct gcagacattc attgttcaac | 2340 |
| ggtttcgatc agatataata attttttgctg aggaaatttg ggaactaatg caattaaggc | 2400 |
| atcttaaact gcccagattt tatttgccag attgcccaag tggatctgtt gacaaaggaa | 2460 |
| ggcacttgga ttttcaaac ttacaaacta tttcttactt gtctccacgt tgttgcacga | 2520 |
| aggaggttat tatggggatt cagaatgtca aaaattagg aatcagtgga ataaggatg | 2580 |
| actataaaag ttttcgggac tctgggcttc ccaacaatct tgtctatctg cagcaacttg | 2640 |
| aaatattgag tcttatatct gttgattata gccttttgcc agtgatcatt tcaagtgcaa | 2700 |
| aagcttttcc agcaacgctc aagaagttga agttggaaag aacttatcta agctggtcat | 2760 |
| acttggacat catagctgag ttgcctaacc ttgaggtgct gaagctgatg gatgacgctt | 2820 |
| gttgtggtga agaatggcat ccaattgtta tgggatttaa tcgattgaag cttttgctaa | 2880 |
| ttaaatatag ttttctcaag tactggaaag ccacaaatga caattttcct gtccttgagc | 2940 |
| gcctcatgat tagaagttgc aaaaatttga aagagatacc cattgagttt gcagatatac | 3000 |
| acacactaca gctgattgag ttaagagagt gtcctcccaa acttggggaa tctgctgcac | 3060 |
| gaattcagaa agaacaagaa gacctcggaa acaaccctgt ggatgttcgt atctcaaatc | 3120 |
| cattgaagga gagtgattct gattcagaag aacattagga aaggatctca aggccagaag | 3180 |
| gattgaactc ttgggatttc atttcggccc tctatcacaa aataccacta aattatcggt | 3240 |
| ttcaagcaat gtgtgacttc caaggagatg tgatatcttt tgtgttgtaa catatttttg | 3300 |
| agttgtactg attcccttct tcccttctct tttatgtaa ctttactaat tcaacttcaa | 3360 |
| gtactagcag accacatggt tgattgtgat cgagtttgat gattattta tacgatgaga | 3420 |
| caaccagttt agaa | 3434 |

<210> SEQ ID NO 43
<211> LENGTH: 3434
<212> TYPE: DNA
<213> ORGANISM: Artificial Sequence
<220> FEATURE:
<223> OTHER INFORMATION: LB junction T-DNA sequence

<400> SEQUENCE: 43
cttcgtcaac atggtggagc acgacacact tgtctactcc aaaaatatca agatacagt        60

```
ctcagaagac caaagggcaa ttgagacttt tcaacaaagg gtaatatccg gaaacctcct    120
cggattccat tgcccagcta tctgtcactt tattgtgaag atagtggaaa aggaaggtgg    180
ctcctacaaa tgccatcatt gcgataaagg aaaggccatc gttgaagatg cctctgccga    240
cagtggtccc aaagatggac ccccacccac gaggagcatc gtggaaaaag aagacgttcc    300
aaccacgtct tcaaagcaag tggattgatg tgatatctcc actgacgtaa gggatgacgc    360
acaatcccac tatccttcgc aagacccttc ctctatataa ggaagttcat ttcatttgga    420
gagaacacgg gggactctag atggctcatg caagtgtggc ttctcttatg agaacaatag    480
aatctctctt gacattcaat tcgccgatgc aatctctatc ctgtgatcac agagaagaac    540
tttgcgctct tcgtgaaaaa gttagttccc tggaagtatt tgtcaagaac tttgagaaaa    600
acaatgtttt tggggaaatg acggattttg aagtagaggt aagagaagtt gcaagtgctg    660
ctgaatacac aattcaactg agactaacag gaactgtact gggagaaaat aaaagccaga    720
aaaaaaaggc gcgtcgaagg tttcgtcaaa gcctgcaaca agtagcagag gacatggatc    780
atatctggaa agagtcgaca aagatccaag ataaaggaaa acaagtatca aaggaatcat    840
tggttcatga ttttttcaagt tcaacaaacg atattttgaa ggttaagaac aatatggttg    900
gacgtgatga tcaaaggaaa cagttgttag aagatctgac tagaagctac tctggggaac    960
ccaaagtcat cccgattgtc gggatgggag catagtgtaa acaaccttta gcaaaagaag   1020
tttacaatga tgaatcaatt ctatgccgtt ttgatgttca tgcctgggct accatatctc   1080
aacagcacaa caaaaggaaa attttgctgg gccttctgca ttccacaatc aaaatggatg   1140
acagggttaa gatgattggt gaagcagagc tagcagacat gttacagaaa agtttaaaga   1200
gaaagaggta cttaattgtc ttggatgata tctggagttg tgaagtgtgg gatggcgtga   1260
gacgatgctt tccaactgaa gacaatgcag ggagtcgaat actgttgact acccgtaatg   1320
atgaagtagc ttgttatgct ggtgtagaga attttttcttt gcggatgagc ttcatggatc   1380
aagatgagag ttggagtctt ttcaaaagtg cagcattttc aagtgaagca ttaccatatg   1440
agttcgagac tgttggaaag caaatcgcag atgaatgtca cgggttacca ctaactattg   1500
tcgtggttgc agggcttctc aaatctaaaa ggacaataga agattggaaa actgttgcta   1560
aagatgtcaa gtcattcgtc acaaatgatc ctgatgaacg atgttcacgt gtgcttgggt   1620
tgagttacga tcacttgaca agcgatctaa aaacatgtct tctgcatttc ggaattttttc   1680 cagaagacag tgatattcca gtgaagaatt tgatgagatc atggatggct gaggggttcc   1740
tgaagttgga aaatgatttg gaaggagagg ttgagaagtg tttgcaagag cttgtcgata   1800
gatgtctagt cctcgtcagc aagagaagtc gagatggaac aaaaattaga tcatgtaagg   1860
ttcatgatct aatatatgac ctgtgcgtga gagaagttca aagggagaac attttttatca   1920 tgaacgacat tgttcttgac gtatcatatc cagaatgttc atatctctgt atgtataaaa   1980
tgcagcccct taagcgcgtg actggtgatg aaattaatta ttgtccctat ggtctttata   2040
gggctcttct taccccctgta aatcgtcagt tgagagatca tgacaacaac aatctttttga   2100 aacgaaccca ttctgttttc tcttttcatc ttgagccttt atattatgtt ctcaaatcag   2160
aggttgttca ttttcaaatta ctcaaagtct tggagctgag acacagacag attgatggtt   2220
tccctcgaga gatactaagc ctcatctggt tgaggtacct atcattgttc agctatggga   2280
atttcgatgt acctccagaa atttgcaggt tatggaatct gcagacattc attgttcaac   2340
ggtttcgatc agatataata atttttgctg aggaaatttg ggaactaatg caattaaggc   2400
```

```
atcttaaact gcccagattt tatttgccag attgcccaag tggatctgtt gacaaaggaa    2460
ggcacttgga ttttcaaac ttacaaacta tttcttactt gtctccacgt tgttgcacga    2520
aggaggttat tatggggatt cagaatgtca aaaattagg aatcagtgga ataaggatg      2580 actataaaag ttttcgggac tctgggcttc ccaacaatct tgtctatctg cagcaacttg    2640
aaatattgag tcttatatct gttgattata gccttttgcc agtgatcatt tcaagtgcaa    2700
aagcttttcc agcaacgctc aagaagttga agttggaaag aacttatcta agctggtcat    2760
acttggacat catagctgag ttgcctaacc ttgaggtgct gaagctgatg gatgacgctt    2820
gttgtggtga agaatggcat ccaattgtta tgggatttaa tcgattgaag cttttgctaa    2880
ttaaatatag ttttctcaag tactggaaag ccacaaatga caattttcct gtccttgagc    2940
gcctcatgat tagaagttgc aaaaatttga aagagatacc cattgagttt gcagatatac    3000
acacactaca gctgattgag ttaagagagt gtcctcccaa acttggggaa tctgctgcac    3060
gaattcagaa agaacaagaa gacctcggaa acaaccctgt ggatgttcgt atctcaaatc    3120
cattgaagga gagtgattct gattcagaag aacattagga aaggatctca aggccagaag    3180
gattgaactc ttgggatttc atttcggccc tctatcacaa aataccacta aattatcggt    3240
ttcaagcaat gtgtgacttc caaggagatg tgatatcttt tgtgttgtaa catatttttg    3300
agttgtactg attcccttct tcccttctct ttttatgtaa ctttactaat tcaacttcaa    3360
gtactagcag accacatggt tgattgtgat cgagtttgat gattatttta tacgatgaga    3420
caaccagttt agaa                                                      3434

<210> SEQ ID NO 44
<211> LENGTH: 3027
<212> TYPE: DNA
<213> ORGANISM: Artificial Sequence
<220> FEATURE:
<223> OTHER INFORMATION: RB junction T-DNA sequence

<400> SEQUENCE: 44
gaaccctgtg gttggcatgc acatacaaat ggacgaacgg ataaaccttt tcacgccctt      60
ttaaatatcc gattattcta ataaacgctc tttctctta ggtttacccg ccaatatatc     120
ctgtcaaaca ctgatagttt aaactgaagg cgggaaacga caatctgatc atgagcggag    180
aattaaggga gtcacgttat gaccccgcc gatgacgcgg gacaagccgt tttacgtttg     240
gaactgacag aaccgcaacg ttgaaggagc cactcagccg cgggtttctg gagtttaatg    300
agctaagcac atacgtcaga aaccattatt gcgcgttcaa aagtcgccta aggtcactat    360
cagctagcaa atatttcttg tcaaaaatgc tccactgacg ttccataaat tcccctcggt    420
atccaattag agtctcatat tcactctcaa tccaaataat ctgcaccgga tctggatcgt    480
ttcgcatgat tgaacaagat ggattgcacg caggttctcc ggccgcttgg gtggagaggc    540
tattcggcta tgactgggca acagacaa tcggctgctc tgatgccgcc gtgttccggc      600
tgtcagcgca ggggcgcccg gttcttttg tcaagaccga cctgtccggt gccctgaatg    660
aactgcagga cgaggcagcg cggctatcgt ggctggccac gacgggcgtt ccttgcgcag    720
ctgtgctcga cgttgtcact gaagcggaa gggactggct gctattgggc gaagtgccgg    780
ggcaggatct cctgtcatct caccttgctc ctgccgagaa agtatccatc atggctgatg    840
caatgcggcg gctgcatacg cttgatccgg ctacctgccc attcgaccac caagcgaaac    900
atcgcatcga gcgagcacgt actcggatgg aagccggtct tgtcgatcag gatgatctgg    960
acgaagagca tcaggggctc gcgccagccg aactgttcgc caggctcaag gcgcgcatgc    1020
```

-continued

```
ccgacggcga tgatctcgtc gtgacccatg gcgatgcctg cttgccgaat atcatggtgg    1080
aaaatggccg cttttctgga ttcatcgact gtggccggct gggtgtggcg gaccgctatc    1140
aggacatagc gttggctacc cgtgatattg ctgaagagct tggcggcgaa tgggctgacc    1200
gcttcctcgt gctttacggt atcgccgctc ccgattcgca gcgcatcgcc ttctatcgcc    1260
ttcttgacga gttcttctga gcgggactct ggggttcgaa atgaccgacc aagcgacgcc    1320
caacctgcca tcacgagatt tcgattccac cgccgcttc tatgaaaggt tgggcttcgg    1380
aatcgttttc cgggacgccg gctggatgat cctccagcgc ggggatctca tgctggagtt    1440
cttcgcccac gggatctctg cggaacaggc ggtcgaaggt gccgatatca ttacgacagc    1500
aacggccgac aagcacaacg ccacgatcct gagcgacaat atgatcgggc ccggcgtcca    1560
catcaacggc gtcggcggcg actgcccagg caagaccgag atgcaccgcg atatcttgct    1620
gcgttcggat attttcgtgg agttcccgcc acagacccgg atgatcccg atcgttcaaa    1680
catttggcaa taaagtttct taagattgaa tcctgttgcc ggtcttgcga tgattatcat    1740
ataatttctg ttgaattacg ttaagcatgt aataattaac atgtaatgca tgacgttatt    1800
tatgagatgg gttttatga ttagagtccc gcaattatac atttaatacg cgatagaaaa    1860
caaaatatag cgcgcaaact aggataaatt atcgcgcgcg gtgtcatcta tgttactaga    1920
tcgggcctcc tgtcaatgct ggcggcggct ctggtggtgg ttctggtggc ggctctgagg    1980
gtggtggctc tgagggtggc ggttctgagg gtggcggctc tgagggaggc ggttccggtg    2040
gtggctctgg ttccggtgat tttgattatg aaaagatggc aaacgctaat aaggggggcta    2100
tgaccgaaaa tgccgatgaa aacgcgctac agtctgacgc taaaggcaaa cttgattctg    2160
tcgctactga ttacggtgct gctatcgatg gtttcattgg tgacgtttcc ggccttgcta    2220
atggtaatgg tgctactggt gattttgctg gctctaattc ccaaatggct caagtcggtg    2280
acggtgataa ttcaccttta atgaataatt tccgtcaata tttaccttcc ctccctcaat    2340
cggttgaatg tcgcccttt gtctttggcc caatacgcaa accgcctctc cccgcgcgtt    2400
ggccgattca ttaatgcagc tggcacgaca ggtttcccga ctggaaagcg ggcagtgagc    2460
gcaacgcaat taatgtgagt tagctcactc attaggcacc ccaggcttta cactttatgc    2520
ttccggctcg tatgttgtgt ggaattgtga gcggataaca atttcacaca ggaaacagct    2580
atgaccatga ttacgccaag cttgcatgcc tgcaggtccc cagattagcc ttttcaattt    2640
cagaaagaat gctaacccac agatggttag agaggcttac gcagcaggtc tcatcaagac    2700
gatctacccg agcaataatc tccaggaaat caaatacctt cccaagaagg ttaaagatgc    2760
agtcaaaaga ttcaggacta actgcatcaa gaacacagag aaagatatat ttctcaagat    2820
cagaagtact attccagtat ggacgattca aggcttgctt cacaaaccaa ggcaagtaat    2880
agagattgga gtctctaaaa aggtagttcc cactgaatca aaggccatgg agtcaaagat    2940
tcaaatagag gacctaacag aactcgccgt aaagactggc gaacagttca tacagagtct    3000
cttacgactc aatgacaaga agaaaat                                         3027
```